United States Patent
Wang et al.

(10) Patent No.: US 12,416,615 B2
(45) Date of Patent: Sep. 16, 2025

(54) METHOD AND APPARATUS FOR METHANE LEAKAGE DETECTION

(71) Applicant: Schlumberger Technology Corporation, Sugar Land, TX (US)

(72) Inventors: Kang Wang, Houston, TX (US); Shu Pan, Calgary (CA); Gocha Chochua, Sugar Land, TX (US); Raphael Gadot, Sugar Land, TX (US); Nasser Ghorbani, Houston, TX (US); Oleg O. Medvedev, Missouri City, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 366 days.

(21) Appl. No.: 18/063,329

(22) Filed: Dec. 8, 2022

(65) Prior Publication Data

US 2023/0176023 A1 Jun. 8, 2023

Related U.S. Application Data

(60) Provisional application No. 63/265,119, filed on Dec. 8, 2021, provisional application No. 63/265,121, filed on Dec. 8, 2021.

(51) Int. Cl.
*G01N 33/00* (2006.01)

(52) U.S. Cl.
CPC ..... *G01N 33/0075* (2013.01); *G01N 33/0034* (2013.01); *G01N 33/0036* (2013.01); *G01N 33/0063* (2013.01); *G01N 33/0068* (2024.05)

(58) Field of Classification Search
CPC .......... G01N 33/0075; G01N 33/0034; G01N 33/0036; G01N 33/0063; G01N 33/0068
See application file for complete search history.

(56) References Cited

U.S. PATENT DOCUMENTS

| | | | | |
|---|---|---|---|---|
| 8,332,063 | B2 * | 12/2012 | Moshier | G06Q 10/06 340/572.1 |
| 8,666,699 | B1 * | 3/2014 | Grube | G08B 13/08 702/182 |

(Continued)

FOREIGN PATENT DOCUMENTS

| | | |
|---|---|---|
| KR | 20150138941 A | 12/2015 |
| KR | 20160008781 A | 1/2016 |

(Continued)

OTHER PUBLICATIONS

Kemp et al., 2021, New Technologiescan Cost-effectively Reduce Oil and 1Gas Methane Emissions,but Policieswill Require Careful2Design to Establish Mitigation Equivalence, published Jan. 22, 2021, non-peer reviewed pre-print submitted to EarthArXiv, downloaded from https://eartharxiv.org/repository/view/2008/ (40 pages).

(Continued)

*Primary Examiner* — Curtis J King
(74) *Attorney, Agent, or Firm* — Jeffrey D. Frantz

(57) ABSTRACT

Systems and methods presented herein generally relate to greenhouse gas emission management and, more particularly, to greenhouse gas emission management systems and methods for performing greenhouse gas detection sensor placement planning, leakage source tracing, and quantification of leakage source detections for oil and gas production facilities.

22 Claims, 17 Drawing Sheets

(56) References Cited

U.S. PATENT DOCUMENTS

| | | | |
|---|---|---|---|
| 9,322,735 B1 | 4/2016 | Tan | |
| 10,677,771 B2* | 6/2020 | Dittberner | G08G 5/55 |
| 11,416,643 B2* | 8/2022 | Daly | G08B 29/18 |
| 11,454,622 B2 | 9/2022 | Billat et al. | |
| 2004/0035179 A1* | 2/2004 | Koch | G08B 29/145 |
| | | | 374/2 |
| 2004/0257227 A1* | 12/2004 | Berry | G21J 5/00 |
| | | | 703/11 |
| 2009/0287520 A1 | 11/2009 | Zimmerman | |
| 2010/0198736 A1 | 8/2010 | Marino | |
| 2010/0268519 A1* | 10/2010 | Henning | G06Q 10/04 |
| | | | 703/6 |
| 2011/0040493 A1 | 2/2011 | Choi et al. | |
| 2011/0063116 A1* | 3/2011 | Lepley | G01N 33/0075 |
| | | | 340/605 |
| 2012/0010917 A1 | 1/2012 | De Godoi | |
| 2013/0246027 A1 | 9/2013 | Rodriguez et al. | |
| 2014/0081579 A1 | 3/2014 | Tyburski | |
| 2015/0185194 A1 | 7/2015 | Prince et al. | |
| 2017/0003684 A1 | 1/2017 | Knudsen | |
| 2017/0097274 A1 | 4/2017 | Thorpe et al. | |
| 2017/0147958 A1 | 5/2017 | Hatfield | |
| 2018/0172544 A1* | 6/2018 | MacMullin | G01F 1/00 |
| 2018/0266240 A1 | 9/2018 | Jaaskelainen | |
| 2018/0266241 A1 | 9/2018 | Ferguson et al. | |
| 2018/0292374 A1 | 10/2018 | Dittberner et al. | |
| 2019/0033160 A1* | 1/2019 | Dittberner | G01M 3/16 |
| 2019/0066479 A1* | 2/2019 | Wesley | G08B 21/16 |
| 2019/0088022 A1* | 3/2019 | Ochiai | G06T 19/006 |
| 2019/0285600 A1 | 9/2019 | Klein et al. | |
| 2019/0366400 A1 | 12/2019 | Chambers | |
| 2019/0386790 A1 | 12/2019 | Hawinkel et al. | |
| 2020/0240259 A1 | 7/2020 | Balasubramaniam et al. | |
| 2020/0320659 A1* | 10/2020 | Whiting | G01M 3/38 |
| 2020/0371079 A1 | 11/2020 | Abedini | |
| 2022/0008972 A1 | 1/2022 | Quigley et al. | |
| 2022/0065834 A1 | 3/2022 | Gadot et al. | |
| 2023/0126546 A1* | 4/2023 | Roy | G01M 3/38 |
| | | | 73/40 |
| 2023/0129412 A1* | 4/2023 | Roy | G01M 3/04 |
| | | | 702/50 |
| 2023/0175914 A1* | 6/2023 | Diven | G01N 33/0065 |
| | | | 73/40.5 A |
| 2024/0201314 A1* | 6/2024 | Gomez-Martinez | G06F 30/20 |

FOREIGN PATENT DOCUMENTS

| | | | |
|---|---|---|---|
| KR | 20200074648 A | 6/2020 | |
| WO | 2016089979 A1 | 6/2016 | |
| WO | 2023033832 A1 | 3/2023 | |
| WO | 2023108041 A1 | 6/2023 | |

OTHER PUBLICATIONS

RSG, What is Responsibly Sourced Gas, https://www.projectcanary.com/responsibly-sourced-gas/, downloaded on Sep. 3, 2021, copyright 2021 (5 pages).

International Search Report and Written Opinion of PCT Application No. PCT/US2021/048981 dated Dec. 23, 2021, 10 pages.

International Search Report and Written Opinion of PCT Application No. PCT/US2021/048977 dated Jun. 3, 2022 9 pages.

International Search Report and Written Opinion of the PCT Application No. PCT/US2022/081142 dated Apr. 25, 2023, 12 pages.

Alvarez, et al. "Assessment of methane emissions from the US oil and gas supply chain." Science 361.6398 (2018): 186-188.

Stockie, John M. "The mathematics of atmospheric dispersion modeling." Siam Review 53.2 (2011): 349-372.

Briggs, G. A. "Optimum formulas for buoyant plume rise." Philosophical Transactions of the Royal Society of London. Series A, Mathematical and Physical Sciences 265.1161 (1969): 197-203.

Hanna et al., Handbook on atmospheric diffusion. No. DOE/TIC-11223. National Oceanic and Atmospheric Administration, Oak Ridge, TN (USA). Atmospheric Turbulence and Diffusion Lab., 1982.

Air Quality Dispersion Modeling—Alternative Models, EPA ISC3 method, https://www.epa.gov/scram/air-quality-dispersion-modeling-alternative-models#isc3 (16 pages).

EMC Other Test Methods, EPA OTM33a method, https://www.epa.gov/emc/emc-other-test-methods#Other%20Test%20Methods (20 pages).

Fugitive Emissions Abatement Simulation Testbed (FEAST) software, https://github.com/EAOgroup/FEAST (6 pages).

Seinfeld, John et al., Atmospheric chemistry and physics: from air pollution to climate change. John Wiley & Sons, 2016, Sections 18.10-18.11, pp. 859-868.

Turner, D. Bruce. Workbook of atmospheric dispersion estimates: an introduction to dispersion modeling. CRC press, 1994, Sections 2.4-2.9, pp. 2-3 to 2-13.

De Visscher, Alex. Air dispersion modeling: foundations and applications. John Wiley & Sons, 2013, sections 6.3-6.5, pp. 145-152.

Ponish, A., et al., 'Some guidelines for genetic algorithm implementation in MINLP batch plant design', Advances in Metaheuristics for Hard Optimization: p. 293., Springer, 2007.

Whitley D., 'Next generation genetic algorithms: A users guide', Handbook of Metaheuristics, Springer, 2019, p. 245-274.

* cited by examiner

METHOD AND APPARATUS FOR METHANE LEAKAGE DETECTION

CROSS REFERENCE TO RELATED APPLICATIONS

This application claims priority from and the benefit of U.S. Provisional Application Ser. No. 63/265,119, entitled "Method and Apparatus for Methane Leakage Detection", Dec. 8, 2021, and U.S. Provisional Application Ser. No. 63/265,121, entitled "Method and Apparatus for Methane Leakage Source location", filed Dec. 8, 2021, each of which is hereby incorporated by reference in its entirety.

BACKGROUND

The present disclosure generally relates to greenhouse gas (GHG) emission monitoring. More particularly, the present disclosure relates to systems and methods to perform methane leakage detection sensor placement, leakage source location, and quantification for oil and gas production facilities.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as an admission of any kind.

Methane is a relatively potent greenhouse gas and the main component of natural gas. The process of extracting and processing natural gas inevitably results in some methane emissions, and those emissions lead to global warming, contributing significantly to climate change. As such, operators in upstream/midstream oil and gas are interested in reducing methane emissions from their facilities. Such emissions arise from a range of facilities (e.g., single wells to gas plant), sources (e.g., intentional vents to unintentional fugitive leaks), and equipment (e.g., tanks, compressors, separators, pneumatic controllers, and so forth). Thus, methane emissions may be reduced by a variety of technologies including leak detection, leak repair, venting elimination, and data management. Indeed, hardware technologies for fugitive leak monitoring include optical gas imaging (OGI), sensor (e.g., GHG sensor) measurement, and some recent novel techniques.

For example, optical gas imaging (OGI) may include a thermal imaging technology using high-sensitivity infrared cameras to detect fugitive gas emissions and has become EPA's recommended method. OGI camera performance may depend on emission rates, environmental conditions and factors including the design, adjustment, and use protocols of the system. Gas sensors may include devices that measure the concentration of a certain gas in one single location positioned near the leak location. Some recent novel techniques may include unmanned inspection of facilities using robots or drones etc. This may reduce labor cost in the long term and may present advantage for scenarios where it is difficult to monitor (DTM) or unsafe to monitor (UTM).

A variety of sensors, cameras and novel technologies may be available in the commercial market, and each may have pros and cons, and comes with different detection range, accuracy and cost. However, on top of the hardware technologies, one challenge is sensor placement planning. In order to monitor gas leakage across a large area or an entire facility (e.g., oil and gas production/processing facility), simply installing the gas sensors without any plan to optimize the sensor deployment will result in an expensive capital cost and no assurance that such deployment would bring encouraging returns. While a site survey may be useful in planning sensor deployment, it may be expensive and not easy to carry out because multiple factors may not be considered in a single site survey, such as wind condition (which varies constantly) and current gas leakage status.

Additionally, another challenge associated with leak detection and repair projects is leak source location and quantification. For instance, when a leakage has been detected by at least one sensor, an inversion model may be used to take real-time GHG gas sensor data, wind condition such as speed and direction as input and produce an interpretation of the probable leak source information, which may include gas leak rate as well as leak location. Such an inversion model may be performed within a digital representation framework (e.g., digital avatar representing monitored facility in a computational environment) in order to create a digital and mathematical model that may be broadly provided as a simulation service. Although many sensors may have their own associated software and method to interpret and quantify the leak source, such methods are often limited and tied up with the specific hardware application.

There is a need to provide a systematic solution, based on numerical modeling, to plan the sensor location for detecting greenhouse gas leakage in an accurate and cost efficient way, such that the plan covers as many potential leak sources in a facility as possible while maintaining economic budget. Furthermore, there is a need to provide systems and methods for leak source quantification to address leak source quantification problems, which may be applicable to a broad range of hardware setup and may be adapted to various gas plume analytical models.

SUMMARY

A summary of certain embodiments described herein is set forth below. It should be noted that these aspects are presented merely to provide the reader with a brief summary of these certain embodiments and that these aspects are not intended to limit the scope of this disclosure.

Certain embodiments of the present disclosure include a method that includes a sensor planning phase wherein a systematic workflow is presented to plan the location of greenhouse gas leakage detection sensors. In embodiments of the disclosure, the detection sensors comprise methane detection sensor and/or Optical Gas Imaging (OGI) cameras. In embodiments of the disclosure, the sensor planning phase comprises interactively guiding sensor placement. In embodiments of the disclosure, interactively guiding sensor placement comprises using one or several of 1) wind rose analysis to determine sensor direction, 2) buoyancy profile to determine sensor elevation, and 3) probability map to determine sensor distance. In embodiments of the disclosure, the method comprises evaluating and comparing a plurality of location plans using one or several of 1) forward simulation with varying leak source, leak date and lagging time, and 2) calculating the plan coverage ratio KPI (key performance indicator).

Certain embodiments of the present disclosure also include an edge device that is part of a cloud-based computing environment. The edge device includes a greenhouse gas emission analysis system configured to analyze environmental data at an oil and gas worksite to plan the location of greenhouse gas leakage detection sensors. The greenhouse gas emission analysis system is also configured to evaluate and compare a plurality of location plans using one or several of 1) forward simulation with varying leak source, leak date and lagging time, and 2) calculating the plan coverage ratio KPI (key performance indicator) . . .

Various refinements of the features noted above may be undertaken in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings, in which.

DETAILED DESCRIPTION

Figure 1:
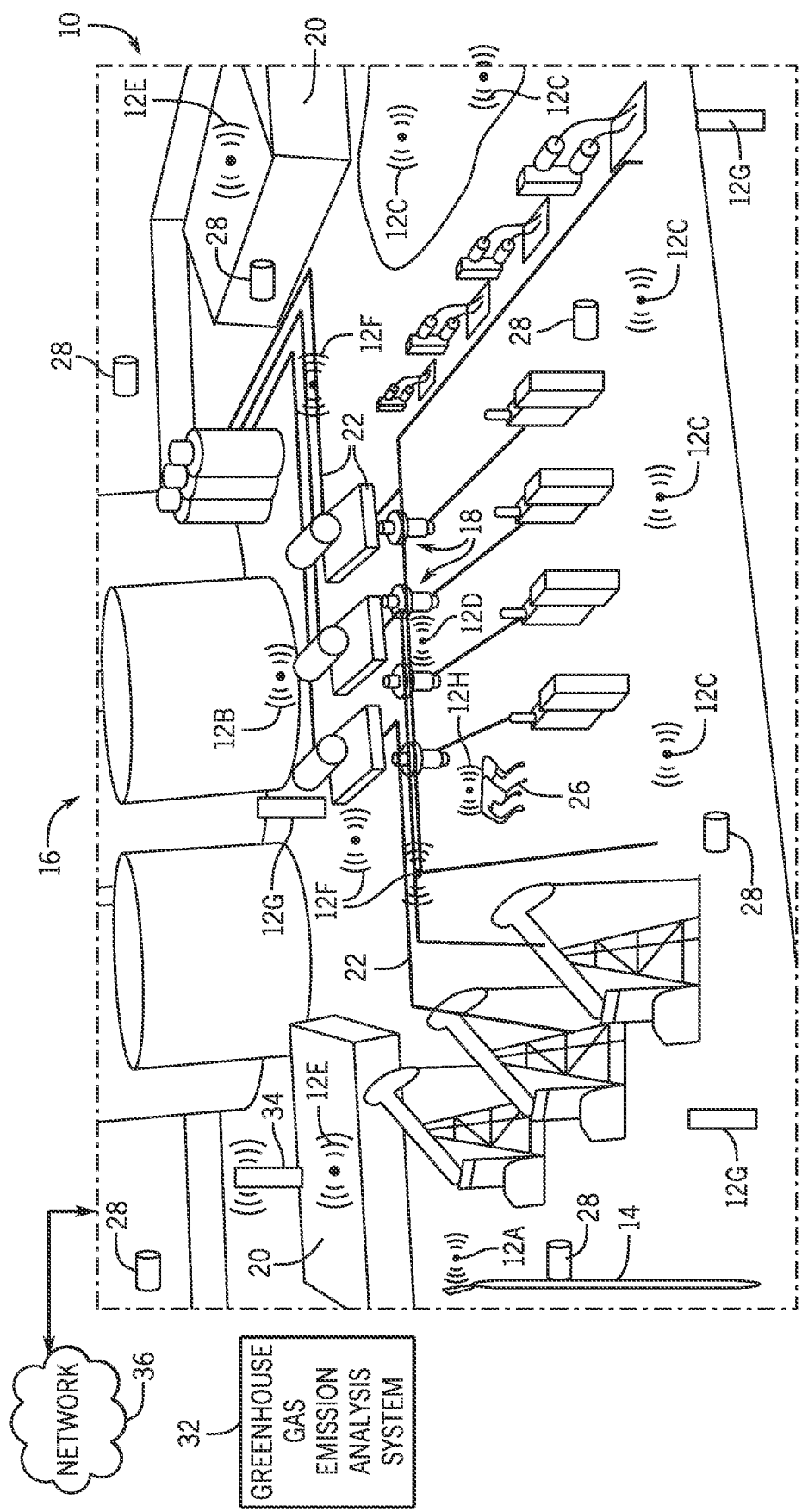
FIG. 1 is an example oil and gas worksite that may include a variety of sensors that may be used to monitor greenhouse gas emissions at the oil and gas worksite, in accordance with embodiments of the present disclosure.

One or more specific embodiments of the present disclosure will be described below. These described embodiments are only examples of the presently disclosed techniques. Additionally, in an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort may be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features.

As used herein, the terms "connect," "connection," "connected," "in connection with," and "connecting" are used to mean "in direct connection with" or "in connection with via one or more elements"; and the term "set" is used to mean "one element" or "more than one element." Further, the terms "couple," "coupling," "coupled," "coupled together," and "coupled with" are used to mean "directly coupled together" or "coupled together via one or more elements."

In addition, as used herein, the terms "real time", "real-time", or "substantially real time" may be used interchangeably and are intended to describe operations (e.g., computing operations) that are performed without any human-perceivable interruption between operations. For example, data relating to the systems described herein may be collected, transmitted, and/or used in control computations in "substantially real time", such that data readings, data transfers, and/or data processing steps may occur once every second, once every 0.1 second, once every 0.01 second, or even more frequent, during operations of the systems (e.g., while the systems are operating). In addition, as used herein, the terms "automatic" and "automated" are intended to describe operations that are performed or are caused to be performed, for example, by a greenhouse gas emission analysis system (i.e., solely by the greenhouse gas emission analysis system, without human intervention).

Aspects of the present disclosure may include enabling the placement of gas leakage detection sensors for oil and gas production facilities. Fugitive emissions of natural gas are economically and environmentally detrimental because emitted gas (e.g., methane that is a main component of natural gas) may be lost from production streams and such gas may include relatively potent greenhouse gas. Certain methods of gas emission detection are relatively expensive and often include either a large amount of work force or expensive equipment to detect gas leaks. Hence, it is desirable to have a systematic solution, based on numerical modeling, to plan the location of gas leakage detection sensors in an accurate and cost efficient way, such that the plan covers as many potential leak sources in a facility (e.g., oil and gas worksites) as possible while maintaining economics. The disclosed embodiments are presented with natural gas (e.g., methane) as one possible example. However, the disclosed embodiments are applicable to gas leakage detection sensors for any suitable gases, including but not limited to carbon oxides ($CO_x$) such as carbon dioxide ($CO_2$) and carbon monoxide (CO), nitrogen oxides (NOx), ozone, other gaseous fuel leaks, or any undesirable gas emissions and/or greenhouse gases.

Other aspects of the present disclosure may include providing systems and methods for leak source quantification to address leak source quantification problems, which may be applicable to a broad range of hardware setups and may be adapted to various gas plume analytical models.

Certain embodiments of the present disclosure include a method that includes a sensor planning phase where a systematic workflow is use to plan the location of greenhouse gas leakage detection sensors. In some embodiments, the detection sensors may include methane detection sensor and/or Optical Gas Imaging (OGI) cameras. In some embodiments, the sensor planning phase may include interactively guiding sensor placement. In some embodiments, interactively guiding sensor placement may include using one or more of 1) a wind rose analysis to determine sensor direction, 2) a buoyancy profile to determine sensor elevation, and 3) a probability map to determine sensor distance. In some embodiments, the sensor planning phase may include evaluating and comparing a set of location plans using one or more of 1) a forward simulation with varying leak source, leak date and lagging time, and 2) calculating the plan coverage ratio KPI (key performance indicator).

Certain embodiments of the present disclosure may include an edge device that is part of a cloud-based computing environment. The edge device may include a greenhouse gas emission analysis system used to analyze environmental data at an oil and gas worksite to facilitating planning and placement of the location of greenhouse gas leakage detection sensors. The greenhouse gas emission analysis system is also used to evaluate and compare different sensor location plans using one or more of 1) forward simulation with varying leak source, leak date and lagging time, and 2) calculating the plan coverage ratio KPI (key performance indicator).

With forgoing in mind, FIG. 1 illustrates an example oil and gas worksite 10 that may include sensors 12 used to monitor greenhouse gas emissions at the oil and gas worksite 10. For example, as illustrated in FIG. 1, in certain embodiments, the sensors 12 may include a variety of sensing devices or monitoring equipment, such as flare monitors 12A (e.g., positioned on top of a tower/post 14), tank sensors 12B (e.g., positioned near gas tanks 16), gas concentration monitors 12C, compressor health monitors 12D (e.g., positioned near compressors 18), structural monitors 12E (e.g., positioned near process facility structures 20), process monitors 12F (e.g., positioned near various pipelines 22), meteorological sensors 12G, and other suitable sensors capable of providing data related to greenhouse gas emissions (e.g., mobile sensors 12H including one or more of the sensors listed above and positioned on a robotic device 26 (e.g., an unmanned vehicle). The sensors 12 may include fluid leak sensors (e.g., gas leak sensors such as methane leak sensors), gas composition sensors, gas specific sensors (e.g., methane sensors), noise or acoustic sensors, flow rate sensors, pressure sensors, wind sensors, temperature sensors, light sensors, flame sensors, or any combination thereof.

In some embodiments, Optical Gas Imaging (OGI) cameras 28 may be used to acquire image data related to greenhouse gas emissions. Such image data may provide additional information associated with the greenhouse gas emissions that may be used to facilitate gas leak detections. The OGI cameras 28 may be deployed in any suitable location within or near the oil and gas worksite 10. For example, the OGI cameras 28 may be positioned on the tower/post 14, at or near locations of the gas tanks 16, compressors 18, process facilities 20, pipelines 22, and so on. In certain embodiments, the sensors 12 and the OGI cameras 28 may be distributed throughout the oil and gas worksite 10 at a plurality of sensor positions (e.g., X, Y, Z coordinates), which may be fixed positions. In some embodiments, the sensors 12 and/or the OGI cameras 28 may be positioned on movable devices, such as the robotic device 26 or other type of robotic devices, or generally arranged in variable positions.

Furthermore, different types of data may be used to monitor greenhouse gas emissions at the oil and gas worksite 10. For example, such data may include location data (e.g., acquired using location sensors associated with the sensors 12 and/or corresponding equipment), time data (e.g., time of day when a detection gas leakage occurred and the sunrise/sunset time on that day), weather data, among other information.

A greenhouse gas emission analysis system 32 may utilize the data acquired by the sensors 12, OGI cameras 28, and the other different types of data (e.g., location data, time data, weather data) based on numerical simulations (e.g., computer-implemented modeling) to plan and evaluate locations of methane (among other gas types) leakage detection sensors (e.g. sensors 12, OGI cameras 28) to enable the leakage detection sensors cover as many potential leak sources in the oil and gas worksite as possible while maintaining desired cost and efficiency. Additionally, the greenhouse gas emission analysis system 32 may provide leak source quantifications that be applied to a broad range of hardware setup and may be adapted to various gas plume analytical models.

In some embodiments, certain equipment/devices may be used to facilitate data collection, processing, and/or transmission. For instance, an edge device 34 may be positioned at or near the oil and gas worksite 10. In some embodiments, the edge device 34 may collect a variety of data (e.g., gas sensor data, image data, location data, time data, and weather data) from different type of data sources that may produce respective data in different data formats. In some embodiments, the edge device 34 may organize (e.g., filter, sort, combine, transform) collected data into a common data pipeline to facilitate data processing and analysis associated with the greenhouse gas emissions that may be used to facilitate gas leak detections.

In some embodiments, one or more digital representations (e.g., computer-implemented simulations) representing a monitored facility (e.g., at the oil and gas worksite 10) in a computational environment may be locally installed in one or more control devices/systems (e.g., gas tank, compressor, and/or pipeline controllers) associated with the oil and gas worksite 10. In some embodiments, the one or more digital representations may be remotely installed in the edge device 34, such that computing resources (e.g., processing circuitry, memory circuitry) of the one or more control devices/systems may be utilized more efficiently for operation control at the oil and gas worksite 10. Moreover, by performing edge computing (e.g., modeling, simulations) at locations near data sources (e.g., the sensors 12, the OGI cameras 28 positioned at the oil and gas worksite 10), use of the edge device 34 may reduce an amount of data to be processed in a site (e.g., remote data center, cloud). Additionally, or alternatively, the edge device 34 may transmit data between a local network (e.g., a network covering the oil and gas worksite 10) and an external network 36 (e.g., cloud). The edge device 34 may translate protocols or languages associated with data and used by local systems or devices into protocols or languages used by the cloud where the data may be further processed.

It should be noted that, for other applications, the particular system, equipment, and devices may be different or specially adapted to the respective application. For example, in some embodiments, the greenhouse gas emission analysis system 32 (or a portion of the system) may be implemented in the edge device 34.

Although described primarily herein as pertaining to a facility (e.g., the oil and gas worksites 10), the term "oil and gas worksite" is intended to include any worksites wherein oil and/or gas is processed in any manner, and from which fugitive gas emissions may occur. Indeed, the embodiments described herein include systems and methods for identifying placement of fugitive gas emissions sensors from any types of worksites including, but not limited to, emissions of natural gas from well pad equipment or any point in delivery of gas to a point of use. In addition, the embodiments described herein may be applied to other types of gases or fluids (e.g., carbon oxides, nitrogen oxides, ozone, and water vapor) emitted from other types of worksites. In general, the embodiments described herein include placing one or more sensors (e.g., sensors 12, OGI cameras 28) at a plurality of sensor positions distributed about an oil and gas worksite 10 as illustrated in FIG. 1. Collectively, the sensors may provide continuous and/or periodic measurements of fugitive and vented greenhouse gas emissions with respect to the oil and gas worksite 10.

Additionally or alternatively, in certain embodiments, one or more of the sensors described herein may be mounted to a mobile platform, such as an unmanned aerial vehicle (e.g., a drone), a mobile robot (e.g., robotic device 26), or any other relatively agile mobile platform configured to move about an oil and gas worksite 10. The mobile platform carrying the one or more sensors may detect relevant data relating to greenhouse gas emissions that may be occurring at the oil and gas worksite 10, as described in greater detail herein.

In certain embodiments, the greenhouse gas sensor position planning system may include a microprocessor, a microcontroller, a processor module or subsystem, a programmable integrated circuit, a programmable gate array, a digital signal processor (DSP), or another control or computing device. Alternatively or additionally, the one or more processors of the greenhouse gas sensor position planning system may include discrete electronic components coupled to a printed circuit board, integrated circuitry (e.g., Application Specific Integrated Circuits (ASIC)), and/or programmable logic devices (e.g., a Field Programmable Gate Arrays (FPGA)).

In certain embodiments, the one or more data models may be implemented as computer program logic for use with the one or more processors of greenhouse gas sensor position planning system. The computer program logic may be embodied in various forms, including a source code form or a computer executable form. Source code may include a series of computer program instructions in a variety of programming languages (e.g., an object code, an assembly language, or a high-level language such as C, C++, or JAVA). The computer instructions may be distributed in any form as a removable storage medium with accompanying printed or electronic documentation (e.g., shrink wrapped software), preloaded on the greenhouse gas emission analysis system 32 (e.g., on system ROM or fixed disk), or distributed from a server or electronic bulletin board over a communication system (e.g., the Internet or World Wide Web). In addition, in certain embodiments, greenhouse gas sensor position planning system may be implemented as an edge device (e.g., the edge device 34) that is part of a cloud-based computing environment, and the computer program logic may be executed by the edge device in the cloud-based computing environment.

Figure 2:
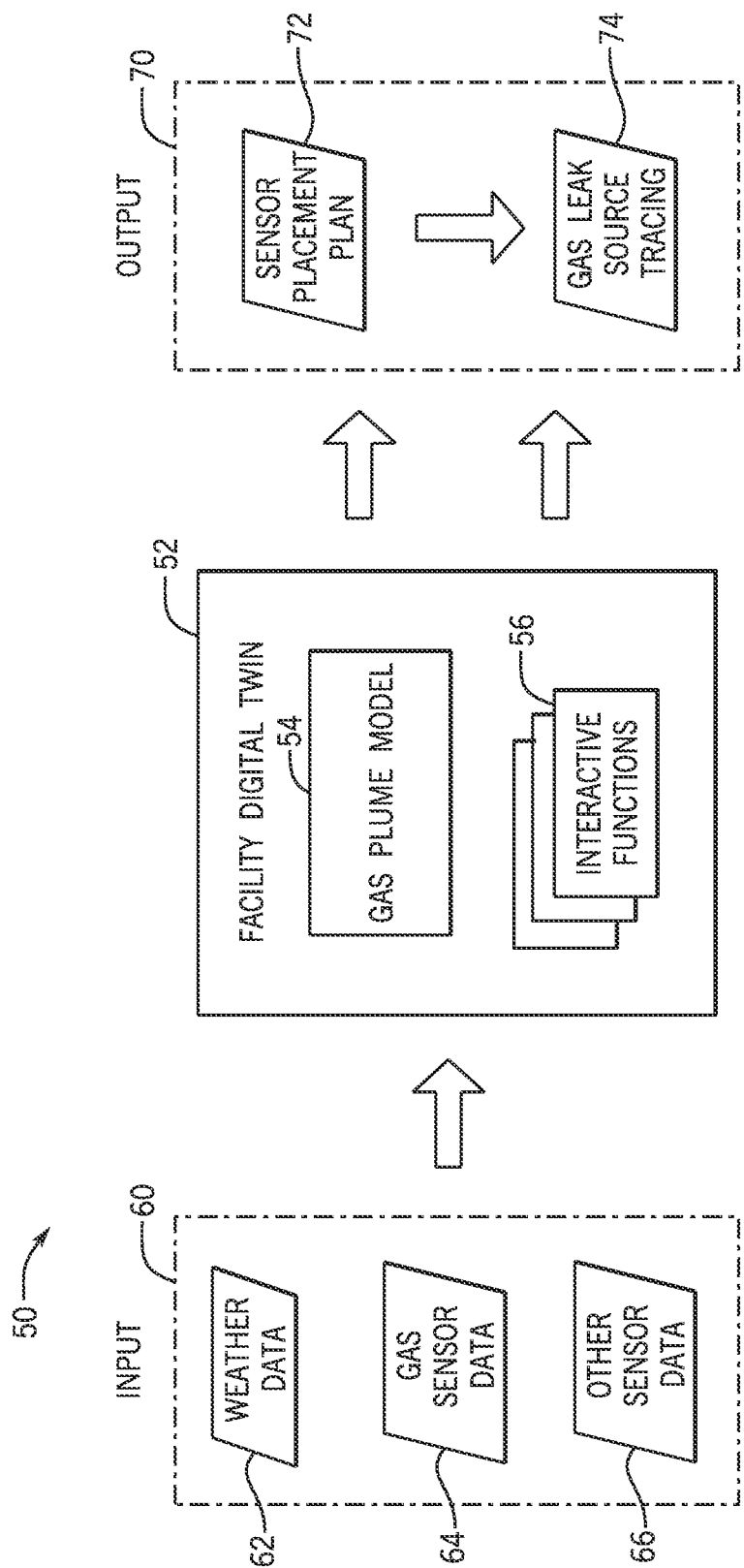
FIG. 2 is a block diagram of a sensor planning design and gas leak source tracing that may be used in the oil and gas worksite of FIG. 1, in accordance with embodiments of the present disclosure.

FIG. 2 is a block diagram of a sensor planning design and gas leak source tracing that may be used in the oil and gas worksite 10 of FIG. 1. A greenhouse gas emission monitoring system 50 may receive input data 60 (e.g., gas sensor data, image data, other relevant data such as location data, time data, weather data) from a variety of date sources, such as the sensors 12, the OGI cameras 28, and location sensors (e.g., GPS sensors) associated with the sensors 12, OGI cameras 28, gas tanks 16, compressors 18, process facilities 20, pipelines 22, network 36, and so on. For instance, the input 60 may include weather data 62, gas sensor data 64, and other sensor data 66 (e.g., image data, location data, and time data). In some embodiments, the input data 60 may be transmitted to a facility digital twin 52 that represents the monitored facility (e.g., at the oil and gas worksite 10) in a computational environment. The term "digital twin" used herein may be referred to as a virtual representation of an object or system that may span a lifecycle of the represented object/system. The "digital twin" may be updated from real-time data (e.g., sensor data), and may use simulation, machine learning and other technologies (e.g., reasoning) to facilitate decision-making related to the object/system. As mentioned previously, in some embodiments, the greenhouse gas emission monitoring system 50 may use the edge device 34 to receive and pre-process (e.g., filtering, sorting, editing, transforming) the input data 60.

In certain cases, the monitored facility (e.g., at the oil and gas worksite 10) may be digitized within a "digital twin" framework under a cloud-based architecture. In some cases, the sensors 12 may include wind sensors positioned in the monitored facility to measure wind speed and direction, among other properties. In some embodiments, the sensors 12 (e.g., gas detection sensors) and/or OGI cameras 28, each with designed accuracies and cost, may be acquired for installation at locations either near a specific equipment (e.g., one of the gas tanks 16, compressors 18, process facilities 20, pipelines 22) or distributed across the monitored facility. The input data 60 from various sensors may then be transmitted to a gas plume analytical model to establish a sensor placement workflow.

For example, the facility digital twin 52 may include a gas plume model 54 and a variety of interactive functions 56. The gas plume model 54 may be generated using various mathematic algorithms associated with data analysis, processing, and simulations related to the gas plume (e.g., plume distribution, gas concentration, gas detection), image processing (e.g., OGI data processing, such as filtering, Fourier transformation, pattern recognition), data correlation (e.g., correlating the gas sensor data 64 and/or image data with the location data, time data, weather data 62), and the like. The interactive functions 56 may provide functionalities (e.g., data mining, numerical calculation, modeling, machine learning, prediction, estimations, error analysis, data visualization) to support the data analysis, processing, and simulations related to the gas plume.

Based on data analysis from the facility digital twin 52, the greenhouse gas emission monitoring system 50 may generate a variety of output data 70. For example, the output data 70 may include one or more sensor placement plans 72, each including a specific sensor (e.g., sensors 12, OGI cameras 28) placement (e.g., a sensor layout map indicative of different sensor type and locations with respect to the oil and gas worksite 10). The sensor layout map may indicate coordinates (e.g., X, Y, and Z) of the sensors in a map of the oil and gas worksite 10, wherein the map may indicate the spatial positioning of various equipment and sensors relative to one another and/or relative to a reference position. The greenhouse gas emission monitoring system 50 may (e.g., using the facility digital twin 52) evaluate the one or more sensor placement plans 72 in a process of gas leak source tracing 74 based on certain criteria, such as coverage ratio, accuracy of gas leak detection, cost, and so on. Additional details with regard to evaluating sensor displacement plans and performing gas leak source tracing will be discussed below with reference to FIGS. 3-15.

Figure 3:
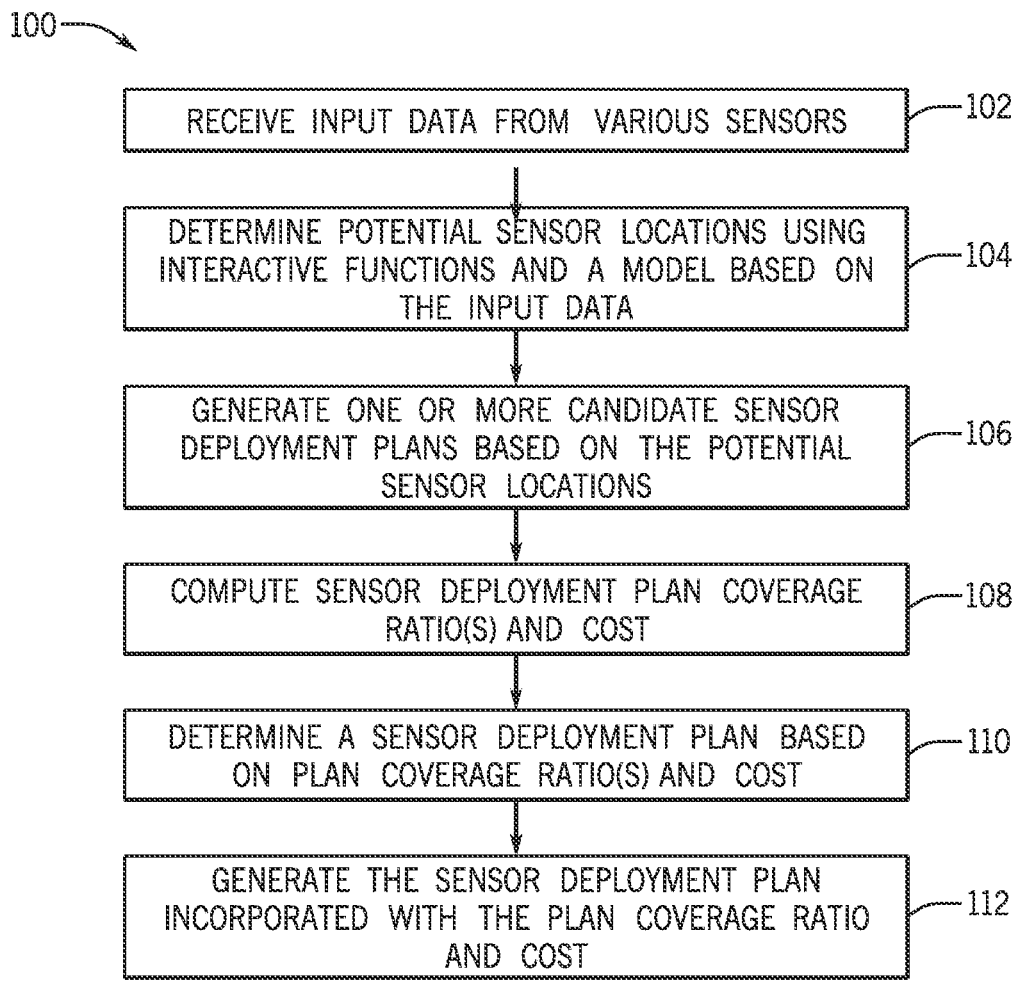
FIG. 3 is a flow chart of an example method for sensor planning that may be used in the sensor planning design and gas leak source tracing of FIG. 2, in accordance with embodiments of the present disclosure.

With the preceding in mind, FIG. 3 is a flow chart of an example method 100 for sensor planning that may be used in the sensor planning design and gas leak source tracing of FIG. 2. In certain embodiments, planning locations of greenhouse gas (e.g., methane) leakage detection sensors (e.g., the sensors 12, OGI cameras 28) includes increasing a sensor coverage (e.g., to cover as many potential leak sources in the monitored facility as possible, while maintaining economic cost). A computing system (e.g., greenhouse gas emission monitoring system 50) may perform operations described below via one or more processors based on processor-executable code stored in one or more memory devices and one or more storage devices. The one or more processors may execute the processor-executable code to perform operations, such as receiving streaming data (e.g., sensor data generated continuously by the sensors 12 and/or OGI cameras 28), querying the industrial devices for datasets associated with the streaming data, generating machine-readable images based on the datasets, embedding the machine-readable images within the streaming data, and sending the streaming data with embedded machine-readable images to a data streaming device. In some embodiments, the operations may include interlacing a buffer of machine-readable images within the streaming data (e.g., consisting of image frames) and retrieving a missing machine-readable image from one or more neighboring image frames.

Although the method 100 described in FIG. 3 is described in a particular order, it should be noted that the method 100 may be performed in any suitable order and is not limited to the order presented herein. Although each processing block is described below in the method 100 as being performed by the computing system (e.g., greenhouse gas emission monitoring system 50), other suitable control systems or devices (e.g., system or devices connected to the greenhouse gas emission monitoring system 50) may perform the methods described herein.

Returning to FIG. 3, at block 102, a computing system receives input data (e.g., input data 60) from various sensors (e.g., sensors 12, OGI cameras 28). The input data may include a geometry of a monitored facility (e.g., a map of the oil and gas worksite 10, including dimensions of various equipment, distances between the equipment, boundaries of the oil and gas worksite 10), wind history data measured prior to planning/deploying the sensors, a list of potential leak sources with location data (e.g., coordinates) and anticipated leak rates, one or more detectable concentration thresholds (e.g., minimum concentration values or ranges) of the sensors, allowed lagging time for gas leakage detection after a leak event occurs, and so on.

At block 104, the computing system may determine potential sensor locations using interactive functions and a model (e.g., computer-implemented model or simulation) based on the input data. For example, the computing system may utilize the interactive functions 56 and gas plume model 54 to analyze, process, and simulate various operations associated with the monitored facility. As mentioned previously, the monitored facility may be digitized to a facility twin (e.g., facility digital twin 52) within a "digital twin" framework under a cloud-based architecture. The facility digital twin 52 may include a gas plume model 54 generated using the interactive functions 56 and other relevant functions and/or algorithms associated with data analysis, data processing, and simulations related to the gas plume monitoring, image data processing, data correlation, and the like.

In some embodiments, the computing system may guide (e.g., via a user interface associate with the computing system) a user (e.g., an operator at the oil and gas worksite 10) regarding suitable sensor positions and times to deploy the sensors based on the interactive functions and the model. For instance, the computing system may use the user interface to guide the user to use a wind rose analysis to determine sensor direction, to use a buoyancy profile to determine sensor elevation, to use a probability map to determine sensor distance (e.g., between sensor and a monitored device/equipment), and so on.

At block 106, the computing system may generate one or more sensor deployment plans based on the potential sensor locations. For example, each sensor deployment plan may include geometries (e.g., a sensor layout map) indicative of different sensor type and locations with respect to a geometry of the monitored facility (e.g., oil and gas worksite 10). Such sensor deployment plans may enable the user to review different options of sensor deployment in an interactive way (e.g., viewing and/or comparing different sensor layout maps via the user interface).

At block 108, the computing system may compute one or more sensor deployment plan coverage ratios and costs associated with respective sensor deployment plans. For example, the computing system may perform sensor deployment plan evaluation. The sensor deployment plan evaluation may include performing simulations (e.g., forward modeling) with varying gas leak sources, leak time, lagging time, and so on. In cases where multiple sensor placement plans are generated (e.g., at block 106), the computing system may calculate a plan coverage ratio and deployment cost for each individual sensor deployment plan.

Based on the computed plan coverage ratios and cost, at block 110, the computing system may determine a sensor deployment plan that may match certain evaluation criteria (e.g., plan accuracy, efficiency, and cost). For example, the computing system may compare different sensor deployment plans to determine the sensor deployment plan based on the evaluation criteria.

At block 112, the computing system may generate the sensor deployment plan incorporated with the plan coverage ratio and cost. That is, the computing system may add the plan coverage ratio and cost into the sensor deployment plan in an interactive manner (e.g., pop up a window with the plan coverage ratio and cost information associated with entire monitored facility and/or individual sensors/cameras when the user move a cursor over the corresponding facility/sensor/camera).

The following sections provide certain mathematic background associated with a gas (e.g., methane) plume analytical model that may enable a fast computation of a gas concentration in the gas leak source tracing. The gas plume analytical model may use input data such as a leak source location with coordinates $(x_s, y_s, z_s)$, a leak rate $Q_s$ (e.g., in volumetric or mass units), and an observation point with coordinates $(x_r, y_r, z_r)$ where a gas concentration is to be determined. The input data may also include an average wind speed $U_{ref}$ and direction $\theta$ measured at a reference height $z_{ref}$ during a given time period $\Delta t$ (e.g., a time period between 5 to 50 minutes, 10 to 60 minutes, 1 to 2 hours, 12 to 24 hours).

The wind direction $\theta$ may be defined as an angle counting from south clockwise. Accordingly, $\theta=0°$ (or) $360°$ represents wind blowing from north, and $\theta=90°$ represents wind blowing from east. In some cases, analytical formulas may assume steady state, so a time interval (e.g., sampling interval) for wind averaging may correspond to an equilibrium time scale (e.g., between 10 minutes and 1 hour). In some embodiments, the sampling interval may be long enough to capture a majority of energy-carrying turbulence eddy scales.

Certain analytical formulas (e.g., sophisticated empirical formulas) may use additional parameters of wind information, such as a standard deviation of the wind direction De and a standard deviation of the wind speed $\sigma_{U_{ref}}$, time of day, daytime solar radiation, nighttime cloud cover, roughness length (a parameter of certain vertical wind profile equations that model the mean wind speed near the ground), terrain type, altitude, temperature, relative humidity, precipitation, albedo, ceiling height, and so on.

The gas plume analytical model may generate output data such as a gas concentration C in ppm (particle per million) at the observation point with coordinates $(x_r, y_r, z_r)$, which may be represented by a gas plume analytical function as indicated below by Equation (1):

$$C(x_r, y_r, z_r) = f(x_s, y_s, z_s, Q_s, U_{ref}, \theta, z_{ref}) \quad (1).$$

Many mathematic options may be available for the gas plume analytical function, such as the Gaussian plume model. However, the disclosed embodiments are not limited to a single set of plume model functions/equations. The gas sensor placement planning and leak tracing method described in the present disclosure may work with any suitable gas plume model with similar input and output and reasonably computation time.

For example, a user may define the input, output, and parameters of the gas sensor placement planning. A gas plume analytical model may be generated to compute a gas (e.g., methane) concentration at an observation point when given a leak source coordinate, leak rate, and average wind speed and direction, as depicted in Equation (1). To setup gas sensor placement planning, the input and output may be expanded to the following:

The input may include a geometry of the monitored facility (e.g., the oil and gas worksite 10). Without loss of generality, a rectangular box (e.g., a geometry grid) may be used as indicated below by Equation (2):

$$\text{GeometryGrid} = (x_{min}, x_{max}, y_{min}, y_{max}, z_{min}, z_{max}, n_x, n_y, n_z) \quad (2),$$

where $x_{min}$ and $x_{max}$ are the minimum and maximum of the rectangular box and $n_x$ is the gridding interval size, both along the x-axis. Wind history measured prior to planning may be expressed as indicated below by Equation (3):

$$\text{WindHistory} = (t_i, U_{ref,i}, \theta_i, z_{ref}), i=1, \ldots, N_w \quad (3),$$

where $N_w$ is the number of wind history records (e.g., 1 year of wind history with 10 minutes interval, such as $N_w \approx 365 \times 24 \times 6 = 52560$).

The input may also include a list of potential leak source coordinates $(x_s, y_s, z_s)$ and anticipated leak rate $Q_s$ that may be expressed as indicated below by Equation (4):

$$\text{PotentialLeakSource} = (x_{si}, y_{si}, z_{si}, Q_{si}), i=1, \ldots, N_{ls} \quad (4),$$

where Nis is the number of the potential leak sources. The coordinates in this list may be predetermined based on geospatial mapping, the facility design diagram (e.g., piping and instrumentation diagram (P&ID)) and field experience. In some embodiments, the anticipated leak rate may be a rough guess or estimate for planning purpose and may be adjusted later in an interactive workflow (e.g., using the method 100).

The input may also include a minimum detectable concentration threshold $C_{min}$ (e.g., 100 ppm, 150 ppm, 200 ppm) may be set for each sensor (e.g., sensors 12, OGI cameras 28). A sensor may show no response below a corresponding minimum detectable concentration threshold $C_{min}$. Additionally, the input may include an allowed lagging time $t_{lag}$ for a gas leak detection after an occurrence of a leak event.

The output may include certain interactive features (e.g., software-related features) that may guide a user to place the sensors (e.g., sensors 12, OGI cameras 28) at desired locations. When there are multiple sensor placement plans, a key performance indicator (KPI) is computed to compare the sensor coverage of each sensor placement plan. For example, the multiple sensor placement plans may include an optimal plan expressed as indicated below by Equation (5):

$$\text{Receptors} = (x_{ri}, y_{ri}, z_{ri}), i=1, \ldots, N_r \quad (5),$$

where $N_r$ is the number of receptors (e.g., sensors 12, OGI cameras 28).

In some cases, users may want to place a sensor relatively close (but not too close) to the potential leak source, such that the sensor may have a capability to cover multiple potential leak sources. In such cases, at least three baseline spatial numbers, including a direction, planar distance, and elevation from a potential leak source may be used to guide the sensor placement. The following sections presents three example methods used in an interactively guided sensor placement process.

In the first example method, a wind rose analysis is used to determine a sensor direction. An example of wind history is given in below in Table 1. Three parameters, including mean wind direction θ, mean wind speed $U_{ref}$, and atmospheric stability class at each time interval are used. Other parameters, such as standard deviation of wind direction $\sigma_\theta$ and standard deviation of wind speed $\sigma_{U_{rer}}$ among others may also be used for determining the stability class, which may represent the category amounting the atmospheric turbulence at a given Earth's location.

TABLE 1

| Time | θ (Mean Wind Direction, degree) | $U_{ref}$ (Mean Wind Speed, m/s) | $\sigma_\theta$ (Std Wind Direction, degree) | $\sigma_{U_{ref}}$ (Std Wind Speed, m/s) | Stability class |
| --- | --- | --- | --- | --- | --- |
| Dec. 31, 2020 23:50 | 243 | 2.2 | 12 | 0.5 | 3 |
| Dec. 31, 2020 23:40 | 236 | 2.3 | 13 | 0.4 | 3 |
| Dec. 31, 2020 23:30 | 245 | 2.8 | 11 | 0.3 | 4 |
| Dec. 31, 2020 23:20 | 254 | 3.0 | 12 | 0.4 | 4 |
| Dec. 31, 2020 23:10 | 239 | 2.1 | 13 | 0.5 | 3 |
| Dec. 31, 2020 23:00 | 273 | 2.4 | 12 | 0.4 | 3 |

In certain embodiments, one full year of wind history (e.g., seasonal and periodic wind behavior) may be obtained by wind measurement. For example, a 10 minutes interval table corresponding to 50,000 measurement points may be displayed using graphic tools (e.g., visualization tools), such as in a wind rose plot, which is a special diagram used by meteorologists to give a succinct view of how wind speed and direction are distributed at a particular location.

Figure 4:
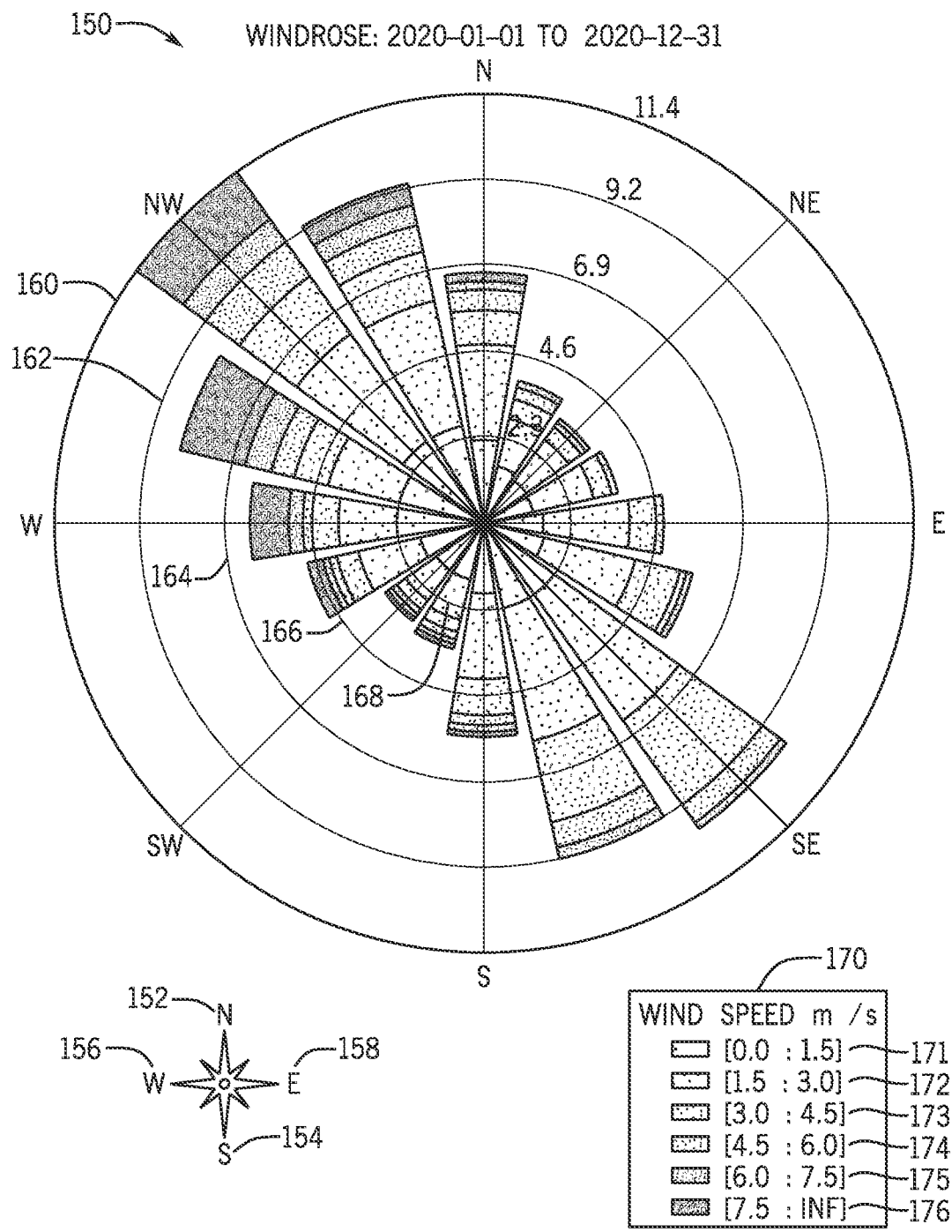
FIG. 4 is an wind rose plot of the Christman Field using data acquired by the Colorado State University, in accordance with embodiments of the present disclosure.

The wind rose plot may give a statistical distribution of desired directions to place the sensors. Such information may be independent of other factors. For example, in some embodiments, a user may download publicly available weather information of a particular field (e.g., the Christman Field measured by Colorado State University), and plot the wind rose map throughout year of 2020 (e.g., as shown in FIG. 4 in later sections). The wind rose plot may indicate the majority of wind blow from certain directions (e.g., NW and SE directions) with a mean wind speed (e.g., 2.7 m/s). In this case, the sensors may be positioned in NW and SE directions to increase (e.g., maximize) probability of detecting gas leaks.

In the second example method, a buoyancy profile analysis is used to determine sensor elevation. The buoyancy profile may be a function of anticipated leak rate $Q_s$ and wind speed U. For example, the gas plume rise may be modeled by a widely used formula developed by Gary Briggs (Briggs, G. A. "Optimum formulas for buoyant plume rise." Philosophical Transactions of the Royal Society of London. Series A, Mathematical and Physical Sciences 265.1161 (1969): 197-203), where Equations (6) and (7) may be used as indicated below:

$$h = z_s + 1.6 F^{\frac{1}{3}} x^{\frac{2}{3}} U^{-1}, \text{ and} \quad (6)$$

$$F = \frac{gQ_s}{\pi}\left(\frac{1}{\rho_M} - \frac{1}{\rho_A}\right). \quad (7)$$

Figure 6:
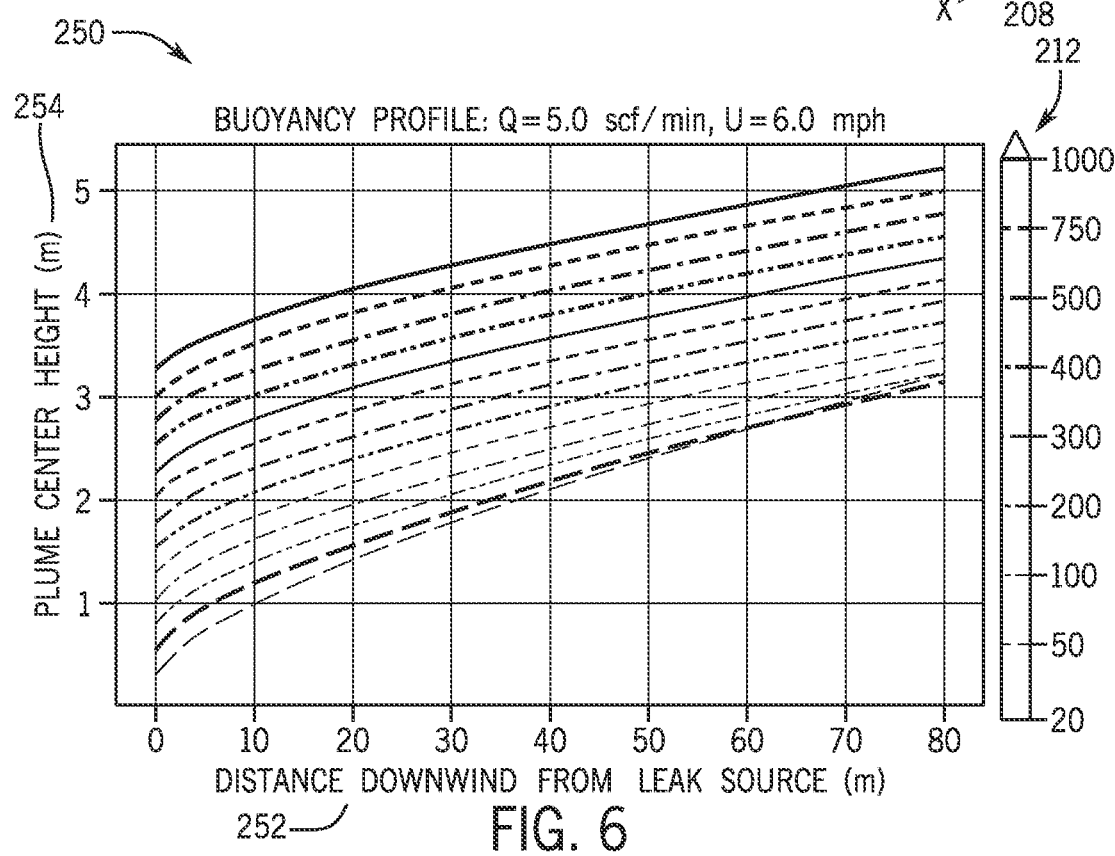
FIG. 6 is an example of a buoyancy profile for a given leakage rate and wind speed, in accordance with embodiments of the present disclosure.

The mean wind speed may be computed based on the wind history data. In the present example, the mean wind speed is 6 mph. If an anticipated leak rate is set at 5 scf/min, a buoyancy profile may be plotted (e.g., as shown in FIG. 6 in later sections). In practice, the buoyancy profile may be helpful in planning a desired sensor elevation above a potential leak source.

In the third example method, a probability of detection map is used to determine sensor distance. For example, a user may define an "ensemble averaged probability of detection" map using the following mathematic equations. At a given a leak source $(x_s, y_s, z_s, Q_s)$, for any grid point $(x_r, y_r, z_r)$, the gas concentration at each time interval $t_i$ may be computed as indicated below by Equation (8):

$$C_i(x_r, y_r, z_r) = f(x_s, y_s, z_s, Q_s, U_{ref_i}, \theta_i, z_{ref}), i=1, \ldots, N_w \quad (8),$$

Equation (8) may be used in combination with the analytical model described previously. The cumulative number of detected time intervals dividing total intervals at any grid point is then calculated by Equation (9) as indicated below:

$$p(x_r, y_r, z_r) = \frac{1}{N_w}\sum_{i=1}^{N_w}[C_i(x_r, y_r, z_r) > C_{min}], \text{ for} \quad (9)$$

$$(x_r, y_r, z_r) \in GeometryGrid,$$

where [S] is the Iverson bracket equal to 1 when statement S is true and 0 when S is false. The ensemble averaged probability of detection is defined by conditional probability, as indicated below by Equation (10):

$$p(x_r, y_r, z_r, t_{lag}) = 1 - (1 - p(x_r, y_r, z_r))^{\frac{t_{lag}}{\Delta t}+1}. \quad (10)$$

For example, if an allowed time of delay $t_{lag}=4$ hours and wind time interval $\Delta t=10$ min, then $P_{lag}=1-(1-p)^{25}$. By looping through all grid points in the GeometryGrid, a 3D probability of detection map may be generated, which serves as an indicator of desired sensor distance. For illustration purpose, a user may use the following parameters:

GeometryGrid=(0m,150m,0m,100m,0m,5.0m,151,101, 51),

WindHistory same as provided above, synthetic leak source $(x_s, y_s, z_s, Q_s)$=(75m,50m,1.0m, 5.0scf/min), $C_{min}$=200ppm,$t_{lag}$=48 hours.

The probability of detection map may be calculated by Equations (8), (9), and (10) and plotted to show, for example, a detectable radius (e.g., 10 meters) with a higher gas leak detection probability on certain directions (e.g., NW and SE directions) at a plane (e.g., at z=1.5 m). The map probability of detection map may indicate similar wind behavior that is consistent with the wind rose plot described above.

In some embodiments, using the interactive tools introduced above, one or more initial sensor placement plans may be generated. For example, based on the GeometryGrid defined previously, a user may create multiple potential leak sources distributed as different groups with identifications (IDs). For each potential leak source, an initial plan may include putting at least one sensor on a direction (e.g., NW/SE direction), a distance (e.g., 5-10 meters) away from the potential leak source, and with an elevation (e.g., 0.5 meter elevation). Using the interactive tool introduced above, multiple sensor placement plans may be generated. Each potential leak source may be marked with a symbol (e.g., star symbol) and each sensor may be marked with a symbol (e.g., downward triangle). The method described herein may include running forward simulation and comparing the coverage ratio KPI (key performance indicator) of each plan.

For example, a forward simulation (e.g., as a function of leak source, leak time, and lagging time) may be used to evaluate each sensor placement plan. The leak source to be simulated may be denoted as $(x_s, y_s, z_s, Q_s)$, leak time as ty, and lagging time as $t_{lag}=t_{l_2}-t_{l_1}$, $l_1$ and $l_2$ are two indexes in the wind history table (e.g., Table 1). The peak concentration between $[t_{l_1}, t_{l_2}]$ at any grid point $(x_r, y_r, z_r) \in$ GeometryGrid may be computed as indicated below by Equation (11):

$$C_{peak}(x_r, y_r, z_r) = \max_{l_1 < i < l_2} f(x_s, y_s, z_s, Q_s, U_{ref_i}, \theta_i, z_{ref}). \quad (11)$$

The peak concentration at each sensor location may also be computed with Equation (11). If $C_{peak}(x_r, y_r, z_r) > C_{min}$, it means the leakage may be detected by sensor i within $t_{lag}$ time since the initial leak.

In addition to the forward simulation, the method described herein may include one or more KPI (key performance indicator) (e.g., a coverage ratio KPI) for evaluating the overall coverage ratio of a candidate plan, as described by Equation (12):

$$\text{Receptors}=(x_{r_j}, y_{r_j}, z_{r_j}), j=1, \ldots, N_r \quad (12).$$

This KPI (key performance indicator) may be used to quantitatively compare alternative plans and identify a desired plan.

The coverage ratio KPI may be calculated as the following: given Nis potential leak sources, corresponding target leak rates, and a sensor location plan, the likelihood of each potential leak source being fully covered by at least one sensor may be computed, then the mean likelihood is the plan's overall coverage ratio.

A formulation for computing coverage ratio may be designed as the following steps: first, for each leak source $(x_{s_i}, y_{s_i}, z_{s_i}, Q_{s_i})$, $i=1, \ldots, N_{ls}$, the probability to have at least one sensor detecting it at any time interval $\Delta t$ is given by the following Equation (13):

$$p_i = \frac{1}{N_w} \sum_{k=1}^{N_w} \left[ \max_{1 \leq j \leq N_r} C_k(x_{r_j}, y_{r_j}, z_{r_j}) > C_{min} \right], i = 1, \ldots, N_{ls}, \quad (13)$$

where $C_k(x_{r_j}, y_{r_j}, z_{r_j})$ is computed same as in Equation (10) at each time interval $t_k$. [S] is the inversion bracket. A similar equation may be constructed for a camera by discretizing the camera area with a list of locations. This probability $p_i$ represents the ratio of time intervals that are detected by at least one sensor out of all intervals. Then, the coverage ratio for leak source i is given by conditional probability as indicated below by Equation (14):

$$r_i = 1 - (1 - p_i)^{\frac{t_{lag}}{\Delta t}+1}, \quad (14)$$

and the plan's overall coverage ratio is given by the following Equation (15):

$$r = 1 - \left(1 - \frac{1}{N_{ls}} \sum_{i=1}^{N_{ls}} p_i\right)^{\frac{t_{lag}}{\Delta t}+1}. \quad (15)$$

In one example, the method described above may apply Equations (13)-(15) to two example plans and yield the coverage ratio $r_i$ for each potential leak source for each plan, as well as the overall coverage ratio r, as indicated below by the additional details in Table 2 and Table 3.

TABLE 2

| Leak Source ID | Plan 01 Coverage Ratio | Plan 02 Coverage Ratio |
| --- | --- | --- |
| LA1 | 99.53% | 92.09% |
| LA2 | 95.87% | 83.89% |
| LA3 | 97.96% | 85.68% |
| LB | 99.28% | 87.28% |
| LC1 | 99.48% | 94.35% |
| LC2 | 99.96% | 98.66% |
| LC3 | 99.17% | 92.64% |
| LD | 99.69% | 92.98% |
| LE1 | 97.40% | 77.09% |
| LE2 | 97.70% | 81.45% |

TABLE 3

| KPI (key performance indicator | Plan 01 | Plan 02 |
| --- | --- | --- |
| Number of sensors | 16 | 8 |
| Overall coverage ratio | 99.20% | 90.85% |

In the present example, Table 2 may be used for iterating and improving the initial plan, as it points out which locations may lack enough coverage. Table 3 illustrates simplistic metrics for making the final decision of an optimal plan.

Figure 10:
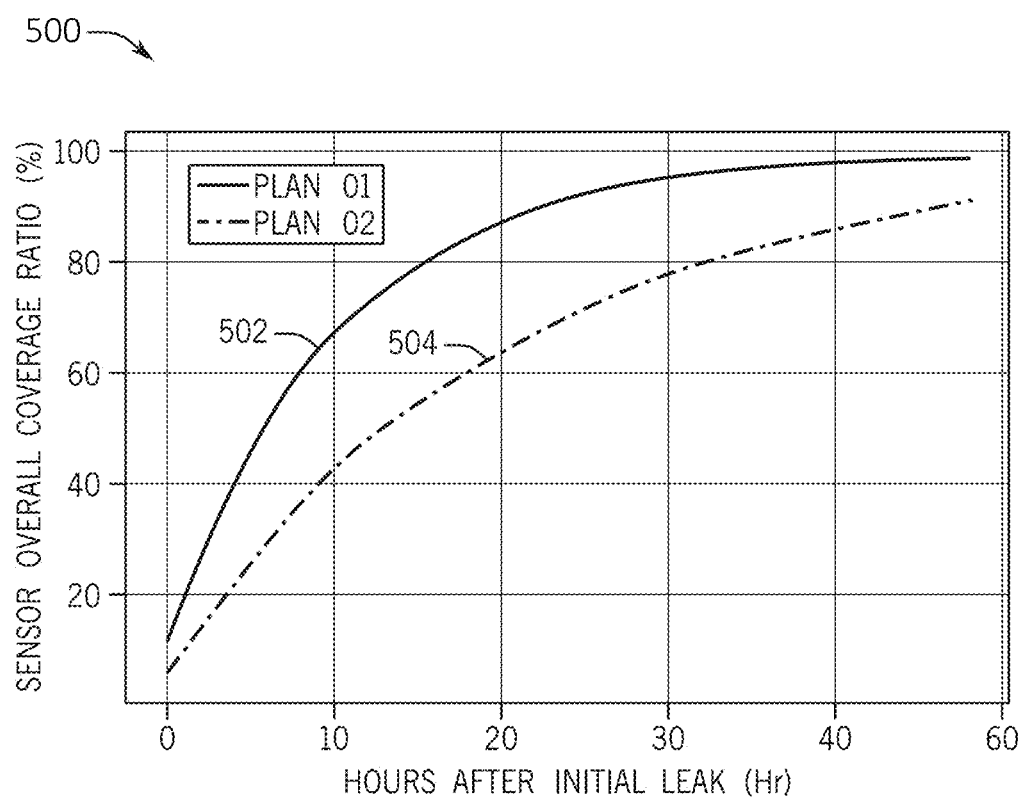
FIG. 10 is an example of sensor overall coverage ratios as functions of time simulated using the gas leakage detection sensor placement plans of FIGS. 8A and 8B after an initial leakage event, in accordance with embodiments of the present disclosure.

In some embodiments, it may also be useful to plot the coverage ratio as a function of time lag, which may give the time varying likelihood of detecting a leakage (e.g., as shown in FIG. 10 in later sections). In the event when a list of potential leak sources may not be available, a "blind coverage ratio" KPI (key performance indicator) may be defined in a similar fashion, by assuming every grid point is a potential leak source. Although this approach may systematically underestimate the actual coverage, it may still be helpful for comparison of alternative plans.

Certain detailed examples, such as wind rose plots, gas concentration distribution plots, buoyancy profiles, ensemble averaged probability of detection maps, gas leakage detection sensor placement plans, and forward simulation of a leak concentration distribution plots may be associated with the example method 100 for sensor planning as discussed in further detail below with reference to FIGS. 4-10.

FIG. 4 is an example of a wind rose plot 150 of the Christman Field using data acquired by the Colorado State University between January to December of year 2020. The wind rose plot 150 may use a coordinate system including North direction 152, South direction 154, West direction 156, and East direction 158. As mentioned above, the wind direction θ may be defined as an angle counting from the South direction 154 clockwise. For instance, θ=0° (or) 360° represents wind blowing from the North direction 152, and θ=90° represents wind blowing from the East direction 158.

In the wind rose plot 150, each radius of a set of circles, such as circles 160, 162, 164, 166, and 168, representing wind speed measurement 170 (e.g., 11.4 m/s, 9.2 m/s, 6.9 m/s, 4.5 m/s, and 2.3 m/s, respectively). Different wind speed measurement values may be indicated with respective speed ranges, such as ranges 171 (wind speed values between 0.0 to 1.5 m/s) to 176 (wind speed values between 7.5 m/s up to infinity).

In the present example, the wind rose plot 150 illustrates a majority of wind blowing from NW and SE directions, with a mean wind speed of 2.7 m/s. In this example, the sensors (e.g., sensors 12) may be positioned in NW and SE directions to increase (e.g., maximize) the probability of detecting gas leaks (e.g., greenhouse gas leaks, such as methane leaks).

Figure 5:
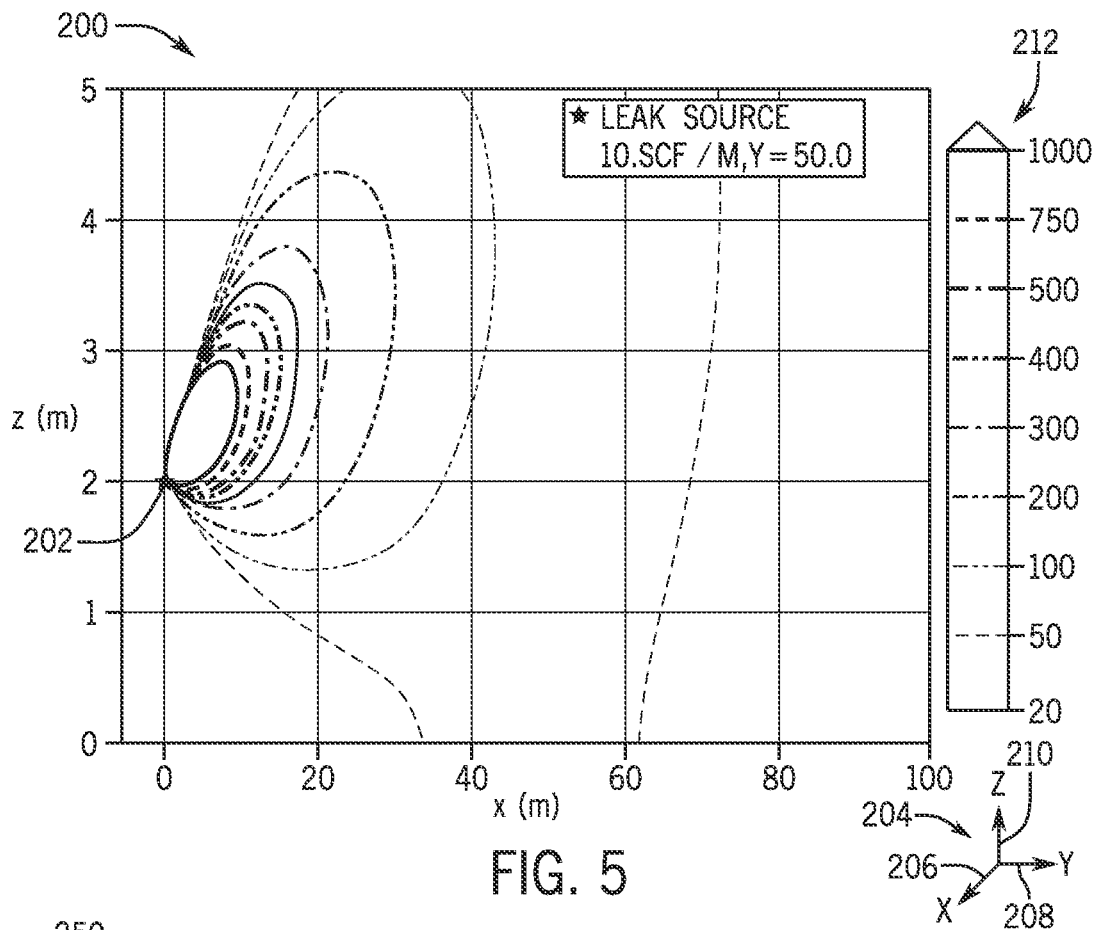
FIG. 5 is an example of a gas concentration distribution plot when buoyancy is considered, in accordance with embodiments of the present disclosure.

FIG. 5 is an example of a gas concentration distribution plot 200 when the buoyancy is considered. The gas concentration distribution plot 200 illustrates a gas plume distribution from a single leak source 202 in a plane having X and Z-axes of a coordinate system 204 at y=50 meters. The coordinate system 204 includes three axes 206 (horizontal axis X), 208 (horizontal axis Y), and 210 (vertical axis Z), each perpendicular to the other two axes. The leak source 202 releases leaking gas at a flow rate of 10.0 SCP/M (in standard cubic feet per minute indicating a molar flow rate of the leaking gas expressed as a volumetric flow at a standardized temperature and pressure).

A Gaussian gas plume model is used to compute the gas concentration distribution plot 200, which displays the calculated extent of the plume distribution in the plane. Each of the illustrated contour lines quantitatively represents a calculated (e.g., using the Gaussian gas plume model) gas concentration profile at locations with respect to the location of the leak source 202. For example, each contour line may represent gas concentration variations (e.g., decreasing) with each contour line further away from the leak source 202. A numerical gas concentration value bar 212 is used herein to indicate different contour line with a corresponding value.

FIG. 6 is an example of a buoyancy profile 250 for a given leakage rate and wind speed. An axis 252 represents distances downwind from the leak source 202 and an axis 254 represents heights of the gas plume center. A mean wind speed may be computed based on the wind history data. In present example, the mean wind speed U=6 mph. If an anticipated leak rate is set (e.g., by a user) at $Q_s$=5.0 scf/minute, the buoyancy profile 250 may be plotted as illustrated in FIG. 6. Each curve in the plot represents a gas plume centerline height variation downwind, where the interception of the curve with the axis 254 is the leak source height $z_s$. The same numerical gas concentration value bar 212 is used herein to indicate different curves with a corresponding value. As illustrated in the buoyancy profile 250, for the given leakage rate ($Q_s$=5.0 scf/m) and wind speed (U=6 mph), the gas plume centerline heights corresponding to different gas concentration values increase with increasing distance downwind from the leak source 202.

The contour plot (e.g., buoyancy profile 250) may be helpful in planning the proper sensor elevation above a potential leak source. For example, the sensor may be positioned at a location 0.5 meter higher when the sensor is at around 10 meters distance from the potential leak source. Once the planar distance is determined, elevation may be automatically adjusted.

Figure 7:
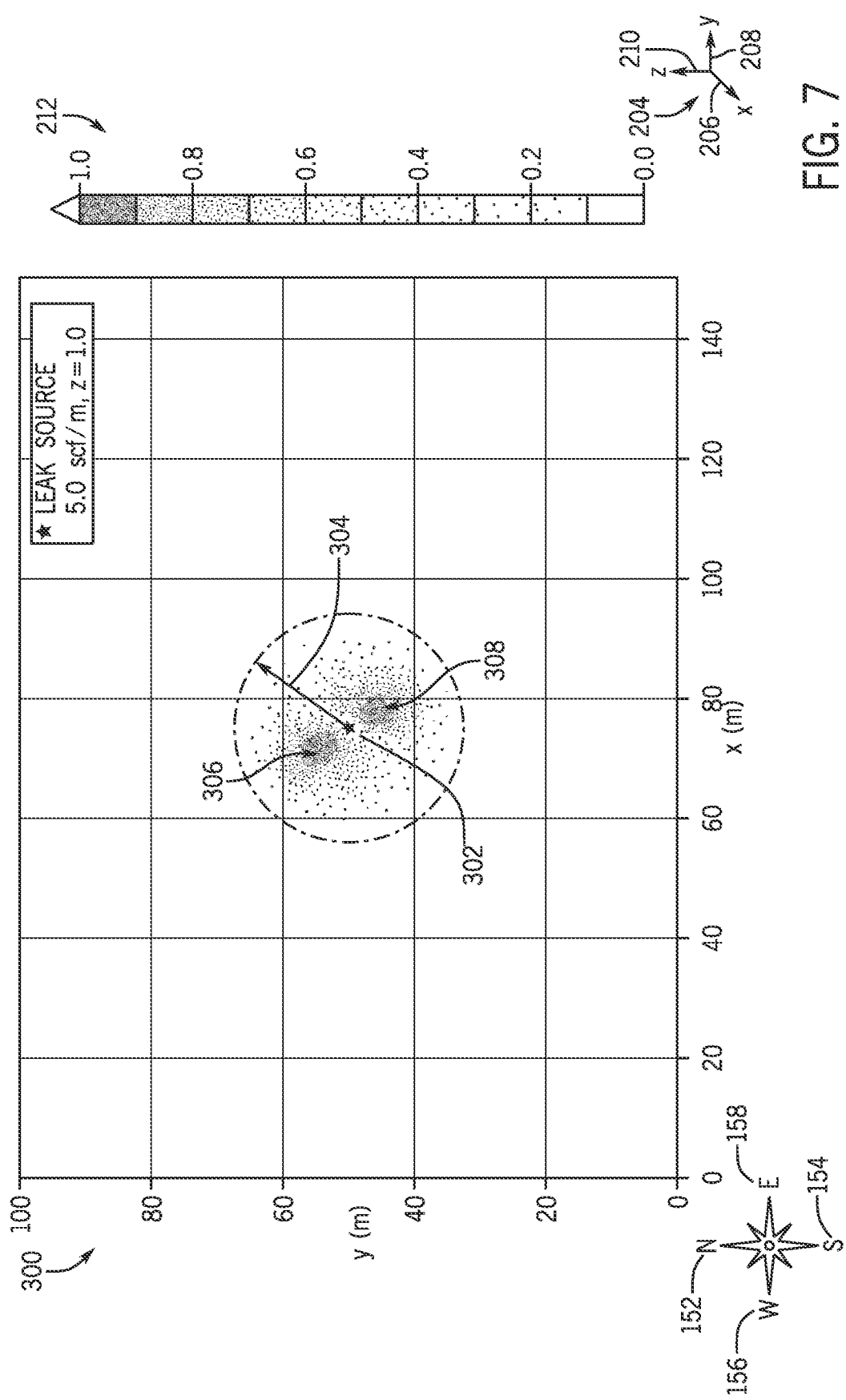
FIG. 7 is an example of an ensemble averaged probability of detection map, in accordance with embodiments of the present disclosure.

FIG. 7 is an example of an ensemble averaged probability of detection map 300. As mentioned previously, a probability of detection map may be calculated by Equations (8) and (9) and plotted for further evaluation. In the present example, the probability of detection map 300 corresponding to a leak source 302 with a flow rate of 5 scf/m is plotted at an X-Y plane at an elevation z=1.5 m. The detection map 300 shows a detectable radius 304 of around 10 m with a higher gas leak detection probability in areas 306 and 308 on NW and SE directions, respectively, which is consistent with the wind rose map 150 of FIG. 4.

As mentioned previously, using the interactive tools introduced above, one or more sensor placement plans may be generated. For example, based on the GeometryGrid defined previously, a user may create 10 potential leak sources distributed as 5 groups A-E with identifications (IDs) as LA1, LA2, LA3, LB, LC1, LC2, LC3, LD, LE1, LE2. For each potential leak source, an initial plan may include putting at least one sensor on a direction (e.g., NW/SE direction), a distance (e.g., 5-10 meters) away from the potential leak source, and with an elevation (e.g., 0.5 meter elevation). Using the interactive tools introduced above, multiple sensor placement plans may be generated. Each potential leak source may be marked with a symbol (e.g., star symbol) and each sensor may be marked with a symbol (e.g., downward triangle). Two examples of gas leakage detection sensor placement plans are given below with respect to FIGS. 8A and 8B.

Figure 8A:
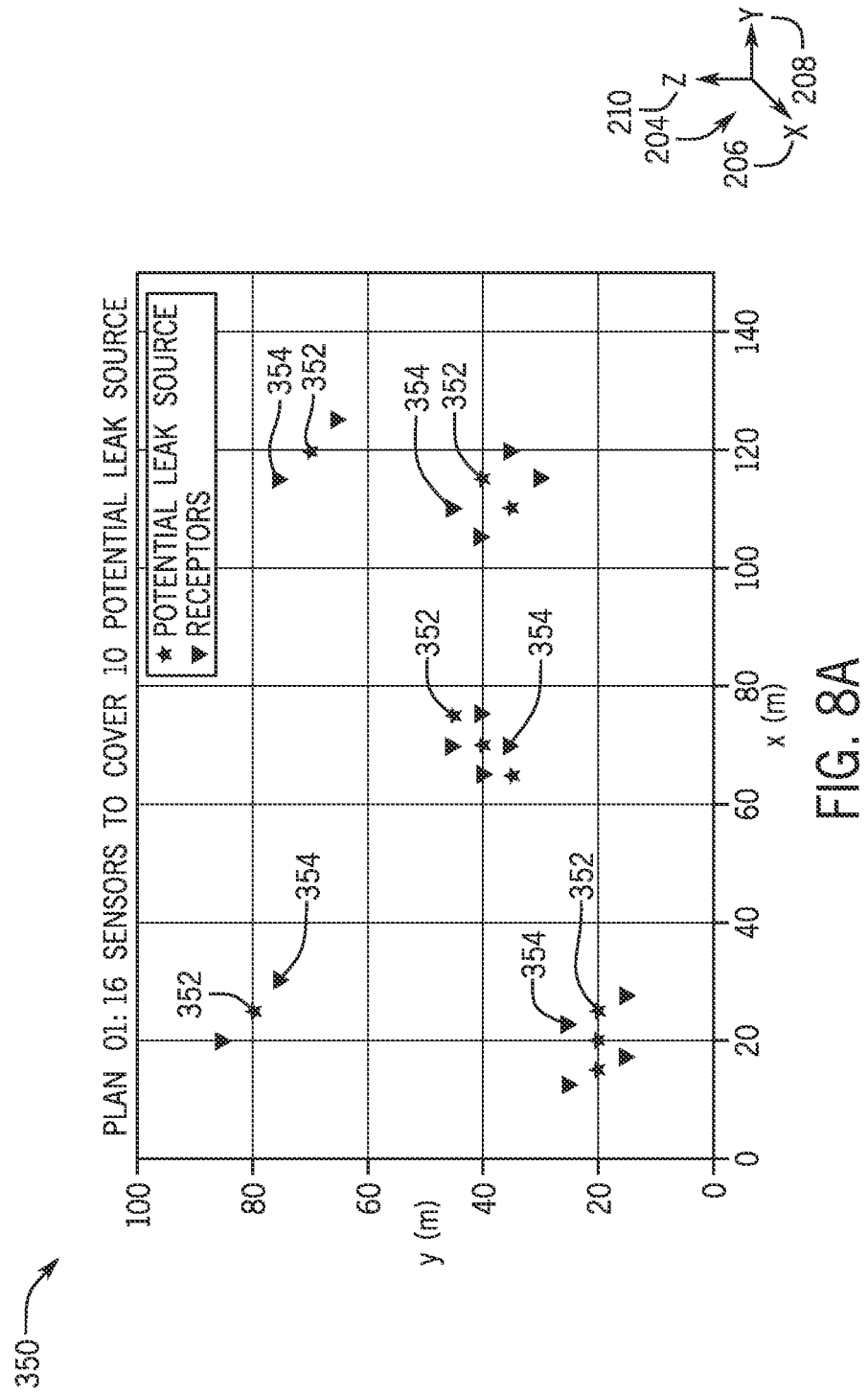
FIG. 8A is an example of a gas leakage detection sensor placement plan that may be used in the sensor planning workflow of FIG. 3, in accordance with embodiments of the present disclosure.

FIG. 8A is an example of a gas leakage detection sensor placement plan 350 that may be used in the sensor planning workflow of FIG. 3. The gas leakage detection sensor placement plan 350 contains 10 potential leak sources 352 (indicated by star symbols) and 16 receptors 354 (e.g., sensors 12, OGI cameras 28, indicated by downward triangles). The lay out of the 10 potential leak sources 352 and 16 receptors 354 is plotted in an X-Y plane. Each sensor is elevated by 0.5 m according to the corresponding equipment group.

Figure 8B:
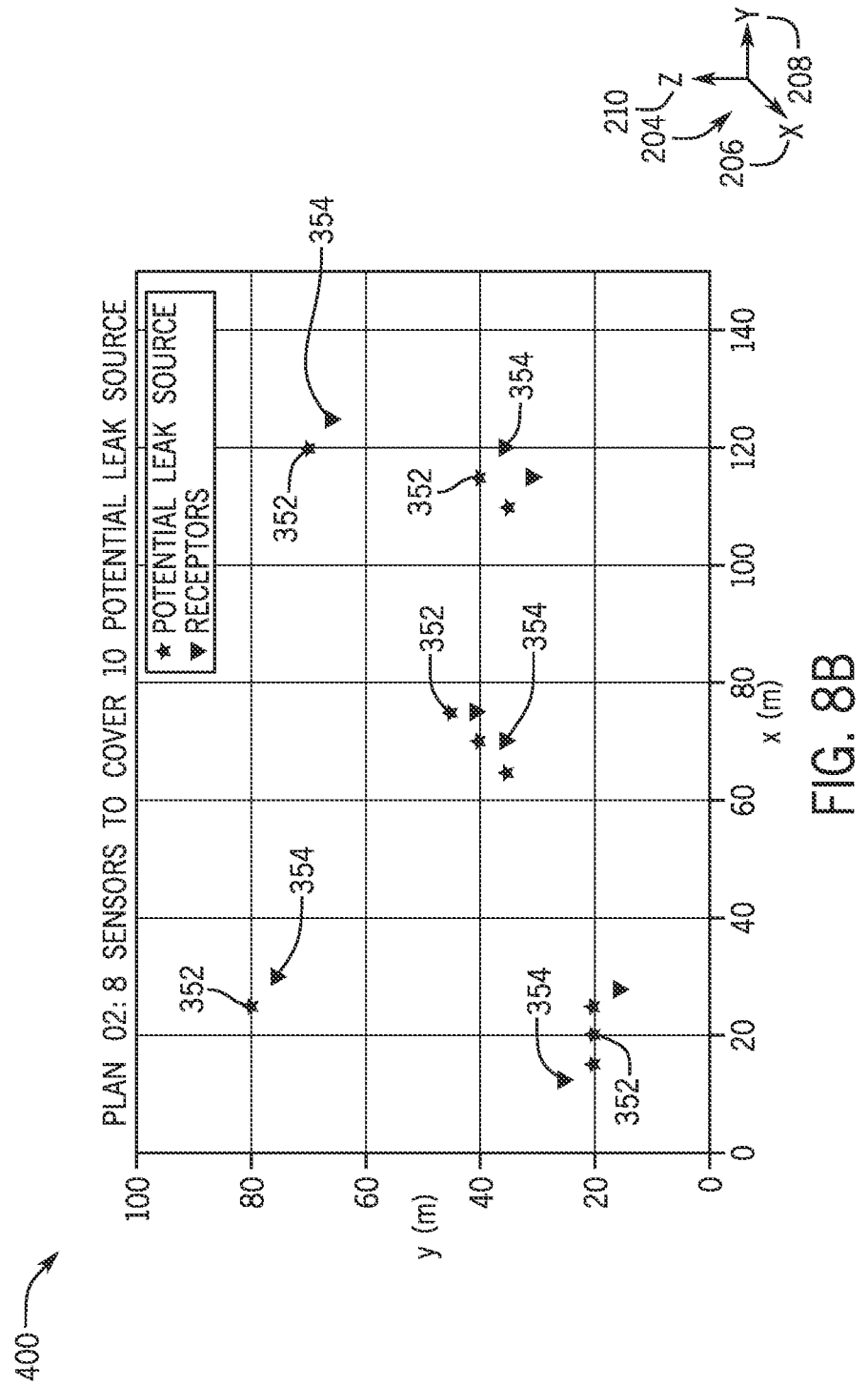
FIG. 8B is another example of a gas leakage detection sensor placement plan that may be used in the sensor planning workflow of FIG. 3, in accordance with embodiments of the present disclosure.

FIG. 8B is another example of a gas leakage detection sensor placement plan 400 that may be used in the sensor planning workflow of FIG. 3. The gas leakage detection sensor placement plan 400 contains 10 potential leak sources 352 (indicated by star symbols) and 8 receptors 354 (e.g., sensors 12, OGI cameras 28, indicated by downward triangles). The lay out of the 10 potential leak sources 352 and 8 receptors 354 is plotted in an X-Y plane. Each sensor is elevated by 0.5 m according to the corresponding equipment group.

The method of generating different gas leakage detection sensor placement plans (e.g., plans 350 and 400) may enable a user to evaluate and compare different plans. The plan evaluation may include running forward simulation and comparing the coverage ratio KPI (key performance indicator) of each plan.

Figure 9:
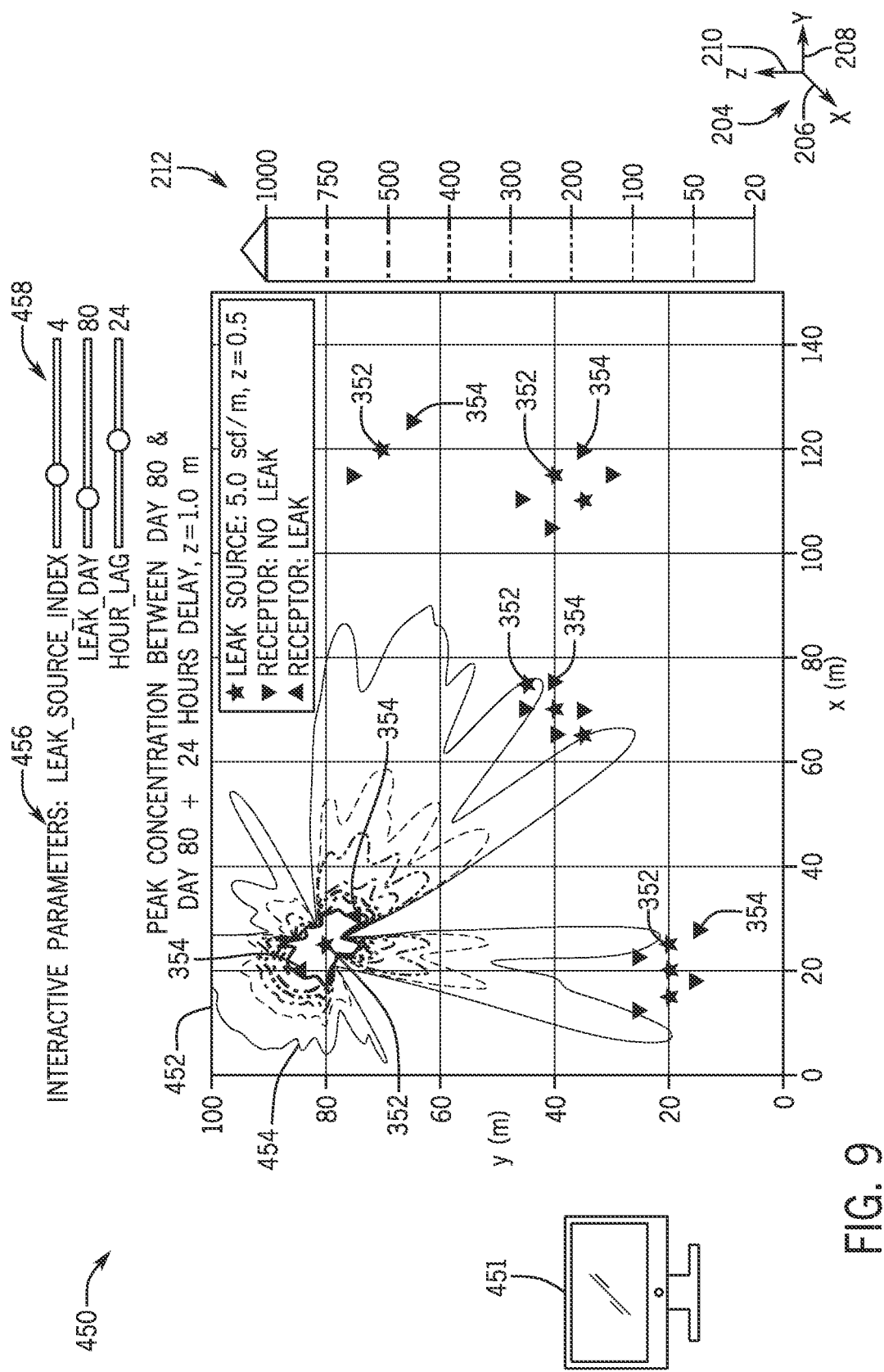
FIG. 9 is an example of a forward simulation of a peak concentration distribution after a leakage event occurs, in accordance with embodiments of the present disclosure.

For example, a forward simulation based on gas leakage detection sensor placement plan 350 may be illustrated by an electronic device 451 having a user interface (UI) 450 in FIG. 9. The electronic device 451 may include a portable or stationary computer (e.g., desktop, laptop, or tablet computer), a smart phone, an electronic display, or a combination thereof. The UI 450 include a display window 452 displaying a forward simulation of a peak concentration distribution plot 454 (similar to the gas concentration distribution plot 200 of FIG. 5) after a leakage event occurs. The peak concentration distribution plot 454 also includes the potential leak sources 352 and receptors 354. The UI 450 also include a set of interactive parameters 456, such as leak_source_index, leak_day, hour lag, and so on. Each of the interactive parameters 456 may be associated with an adjustable bar 458 that may enable a user to adjust the corresponding interactive parameter 456.

For example, using the UI 450, the user may interactively change the leak source ID, leak time (e.g., leak_day) and lagging time (hour_lag), and view the corresponding peak concentration distribution instantaneously. The peak concentration distribution may include the contour plot (peak concentration distribution plot 454) generated from grid points evaluation, as well as the concentration at each sensor location as shown by the text next to the sensor IDs. If a sensor is detected having a leak, the downward triangle is changed to an upward triangle. For an OGI camera 28, if any location within the area of the camera has an excessive concentration, the camera is determined to capture (e.g., image) a detected leak.

In some embodiments, it may also be useful to plot the coverage ratio as a function of time lag, which may give the time varying likelihood of detecting a leakage. FIG. 10 is an example of a sensor overall coverage ratio plot 500 as a function of time simulated using the gas leakage detection sensor placement plan 350 of FIG. 8A and plan 400 of FIG. 8B after an initial leakage event. A profile or curve 502 represents sensor overall coverage ratio corresponding to the gas leakage detection sensor placement plan 350, and another profile or curve 504 represents sensor overall coverage ratio corresponding to the gas leakage detection sensor placement plan 400. Based on the sensor overall coverage ratio plot 500, the gas leakage detection sensor placement plan 350, when implemented in a facility, may result in better performance (e.g., better gas leak detection) than gas leakage detection sensor placement plan 400 because of the higher sensor overall coverage ratio of the gas leakage detection sensor placement plan 350.

In the event when a list of potential leak sources may not be available, a "blind coverage ratio" KPI (key performance indicator) may be defined in a similar fashion, by assuming every grid point is a potential leak source. Although this approach may systematically underestimate the actual coverage, it may still be helpful for comparison of alternative plans.

The preceding sections describe the sensor planning phase that may include, for example, evaluating and comparing a set of sensor placement plans using the forward simulation with varying leak source, leak date and lagging time, and calculating the plan coverage ratio KPI (key performance indicator). A gas leak source tracing phase may follow the sensor planning phase. For example, after deploying the sensors (e.g., sensors 12, OGI cameras 28) in a facility (e.g., at the oil and gas worksite 10), a system (e.g., greenhouse gas emission monitoring system 50) may use various sensor data (e.g., gas sensor data 64, other sensor data 66) and other relevant data (e.g., weather data 62) to perform the gas leak source tracing for locating gas leak sources.

For example, in one embodiment, the greenhouse gas emission monitoring system 50 may enable a gas (e.g., methane) leak source tracing process to trace the leak source location, leak gas flow rate, and other aspects (e.g., wind direction) related to a gas leakage detected by at least one sensor (e.g., one of the sensors 12 or OGI cameras 28). For instance, a certain time period (e.g., 30 minutes, 1 hour, 2 hours, 3 hours, 5 hours) after the gas leakage occurred, one or more sensors may generate a reading (e.g., gas concentration measurement) that is above a threshold concentration of the gas at one or more sensor monitoring locations. The greenhouse gas emission monitoring system 50 may use one or more effective readings to trace back the gas leak source (e.g., location of the gas leakage). In some cases, the gas leak source tracing may yield certain errors caused by a model mismatch, data accuracy, and so on.

The gas leak source tracing process may use input data via a data collection that collects a variety of data. The collect data may include effective concentration measurements $\tilde{C}_i \leq C$ $(x_i, y_i, z_i)$, i=1, . . . n, where $\tilde{C}_i > C_{min}$, which is a minimum detectable concentration threshold. The measurement accuracy may be specified as $|C(x_i, y_i, z_i) - \tilde{C}_i|$. The collected data may also include a time stamp $t_i$ corresponding to each effective measurement, as well as wind conditions (e.g., wind speed $U_i$, and wind direction $\theta_i$) at the time stamp $t_i$. Furthermore, the collected data may include a list of potential leak source coordinates $(x_{s_i}, y_{s_i}, z_{s_i})$, i=1, . . . , $N_{ls}$.

The gas leak source tracing process may generate output data. The output data may include leak source coordinates $(x_s, y_s, z_s)$ and leak rate $Q_s$ that may match (e.g., based on fittings) the concentration measurements. For example, based on Equation (1), a general gas plume analytical function may be expressed as indicated below by Equation (16):

$$C(x_i, y_i, z_i) = f(x_s, y_s, z_s, Q_s, U_i, \theta_i), i=1, \ldots n \quad (16).$$

In a least squares sense, solving the gas concentration C may be written as indicated below by Equation (17):

$$\text{given } x_i, y_i, z_i, U_i, \theta_i, \tilde{C}_i, i=1, \ldots, n, \text{find} x_s, y_s, z_s, Q_s,$$

$$\text{s.t.} \sum_{i=1}^{n} (C(x_i, y_i, z_i) - \tilde{C}_i)^2 \text{ is minimized.} \quad (17).$$

Besides $L^2$ norm used in Equation (17), other forms of minimization functions may also be used.

Based on Equations (16) and (17), the gas leak source tracing process may include performing a naïve 4-parameter $(x_s, y_s, z_s, Q_s)$ optimization, using suitable optimization algorithms, such as Levenberg-Marquardt, gradient descent, trust-region, BFGS, etc. The gas leak source tracing process may also include defining the function f in Equation (16), specifying the optimization of 4-parameter $(x_s, y_s, z_s, Q_s)$, and substituting the measurement data (e.g., gas sensor data, camera image data) to the optimization. The resulting parameters include the optimized values in the sense of minimizing sum of the squared residuals of simulated versus measured concentration.

In some cases, the optimization may converge to a local minimum instead of a global minimum. In some cases, the optimization may not find a minimum. Alternatively, a different and robust method may be used to incorporate a-priori knowledge on the coordinates of a list of potential leak sources that may be identified, for example, based on historical data (e.g., history of gas leakages being detected), synthetic data (e.g., simulation data by modeling various gas leakage events), or the like.

Figure 11:
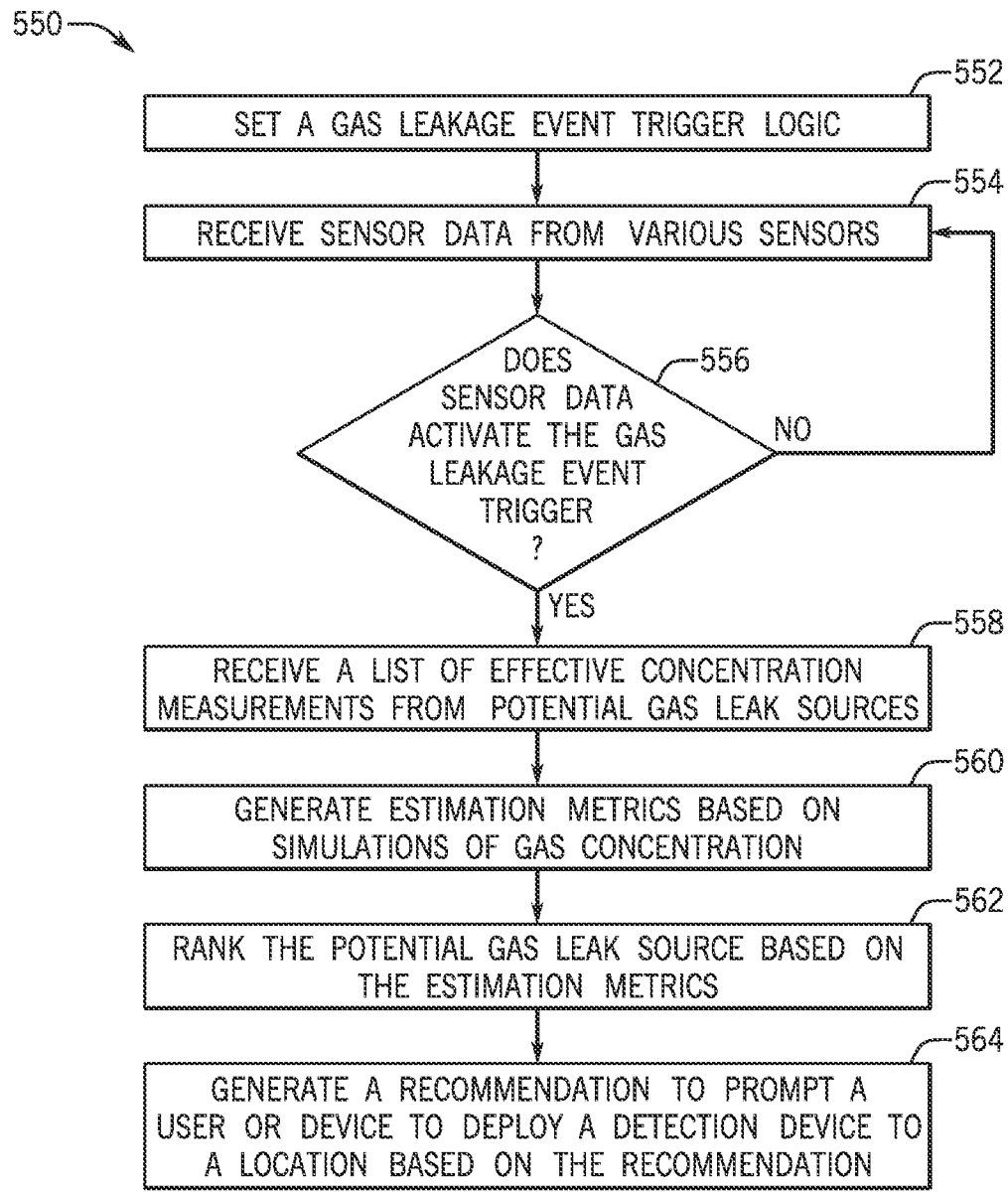
FIG. 11 is a flow chart of an example method for gas leak source tracing that may be used in the sensor planning design and gas leak source tracing of FIG. 2, in accordance with embodiments of the present disclosure.

With the preceding in mind, FIG. 11 is a flow chart of an example method 550 for gas leak source tracing that may be used in the sensor planning design and gas leak source tracing of FIG. 2. A computing system (e.g., greenhouse gas emission monitoring system 50) may perform operations described below via one or more processors based on processor-executable code stored in one or more memory devices and one or more storage devices. The one or more processors may execute the processor-executable code to perform operations, such as receiving streaming data (e.g., sensor data generated continuously by the sensors 12 and/or OGI cameras 28), querying the industrial devices for datasets associated with the streaming data, generating machine-readable images based on the datasets, embedding the machine-readable images within the streaming data, and sending the streaming data with embedded machine-readable images to a data streaming device. In some embodiments, the operations may include interlacing a buffer of machine-readable images within the streaming data (e.g., including image frames) and retrieving a missing machine-readable image from one or more neighboring image frames.

Although the method 550 described in FIG. 11 is described in a particular order, it should be noted that the method 550 may be performed in any suitable order and is not limited to the order presented herein. It should also be noted that although each processing block is described below in the method 550 as being performed by the computing system (e.g., greenhouse gas emission monitoring system 50), other suitable control systems or devices (e.g., system or devices connected to the greenhouse gas emission monitoring system 50) may perform the methods described herein.

Returning to FIG. 11, at block 552, the computing system may set a gas leakage event trigger logic. For example, during a sensor (e.g., sensors 12, OGI cameras 28) setting phase for each individual sensor, a gas leakage event trigger logic may be set (e.g., in hardware, software, or a combination thereof). When a reading (e.g., gas concentration measurement) of the sensor is above a threshold concentration (e.g., a minimum detectable concentration threshold), the computing system may automatically trigger a gas leak source tracing.

After setting the gas leakage event trigger logic for each sensor, at block 554, the computing system may receive sensor data from various sensors, such as the sensors 12, OGI cameras 28, and/or other suitable sensors that may provide sensing data related to gas leak detection. As mentioned previously, the computing system may utilize an edge device (e.g., edge device 34) to collect a variety of data (e.g., gas sensor data, image data, location data, time data, weather data) from different type of data sources that may produce respective data in different data formats. In some embodiments, the edge device 34 may organize (e.g., filter, sort, combine, transform) collected data into a common data pipeline to facilitate data processing and analysis associated with the greenhouse gas emissions that may be used to facilitate gas leak detections.

After data collection, at block 556, the computing system may determine whether the sensor data activates a gas leakage event trigger. The computing system may utilize a digital representation (e.g., the facility digital twin 52 that represents a monitored facility (e.g., at the oil and gas worksite 10) in a computational environment) to help make the determination. In some embodiments, the computing system or a portion of the computing system (e.g., the digital representation) may be implemented in the edge device 34 to facilitate receiving and processing (e.g., data filtering, sorting, editing, transforming, analysis, modeling, prediction) using the sensor data.

If the computing system determines that the sensor data activates the gas leakage event trigger (e.g., a gas concentration measurement of a sensor is above a minimum detectable concentration threshold), at block 558, the computing system may receive a list of effective gas concentration measurements from potential gas leak sources. For example, the process may loop for all potential leak sources, pretending as if the potential leak sources (e.g., with index k=1, 2, 3, . . . . Nis) are actual leak sources. The list of effective gas concentration measurements may include sensor location data, effective concentration measurements $\tilde{C}_i$ associated with time stamp $t_i$ corresponding to each effective measurement, as well as wind conditions (e.g., wind speed $U_i$, and wind direction $\theta_i$) at the time stamp $t_i$, a list of potential leak source coordinates $(x_{s_i}, y_{s_i}, z_{s_i})$, and so on. The potential gas leak sources may be determined (e.g., using the digital representation) based on historical data (e.g., history of gas leakages being detected), synthetic data (e.g., simulation data by modeling various gas leakage events), or the like.

If the computing system determines that the sensor data does not activate the gas leakage event trigger (e.g., a gas concentration measurement of a sensor is below a minimum detectable concentration threshold), the computing system may continue receiving updated sensor data from the various sensors.

At block 560, the computing system may generate estimation metrics based on simulations of gas concentration. For instance, the computing system may solve (e.g., using the digital representation) an optimization problem (e.g., optimizing naïve 4-parameter $(x_s, y_s, z_s, Q_s)$) using simulations based on methods described above with respect to Equations (16) and (17). Solving the optimization problem may include defining the function f in Equation (16), specifying the optimization of 4-parameter $(x_s, y_s, z_s, Q_s)$, and substituting the measurement data (e.g., gas sensor data, camera image data) to the optimization. The resulting parameters (e.g., parameter estimations) may include the optimized values in the sense of minimizing sum of the squared residuals of simulated versus measured concentration.

In some embodiments, solving the optimization problem may include optimizing the 4-parameter $(x_s, y_s, z_s, Q_s)$. In some cases (e.g., with a-priori knowledge on the coordinates $(x_s, y_s, z_s)$ of a list of potential leak sources), solving the optimization problem may include optimizing only one parameter, the leakage rate $Q_s$.

For each estimation (e.g., estimated parameter, $x_s$, $y_s$, $z_s$, or $Q_s$), the computing system may generate the estimation metrics based on simulated versus measured concentration. A variety of estimation metrics may be used. In some embodiments, regression metrics may be used to implement several loss, score, and utility functions to measure regression performance. In some embodiments, $R^2$ goodness-of-fit indicator may be used.

After generating estimation metrics, at block 562, the computing system may rank the potential gas leak sources based on the estimation metrics. For example, the computing system may use the estimation metrics to sort the potential gas leak sources and generate a ranking list, where one or more candidates (e.g., top three gas leak sources) along with the estimations (e.g., estimated leakage rate $Q_s$) may be used as final leak source tracing result.

At block 564, the computing system may generate a recommendation to prompt a user (e.g., a field engineer) or device (e.g., a robotic device) to deploy a detection device (e.g., one of the sensors 12 or OGI cameras 28) to a location based on the recommendation. The recommendation may include the location(s) associated with the one or more candidates (e.g., top three gas leak sources). The user or the device may carry the detection device to each location to perform data measurement and validate the gas leakage based on the data measurement. The user or the device may further perform certain actions to fix the gas leakage (e.g., closing valves, shutting down power supply to equipment associated with the gas leakage). The gas leakage event may be recorded in a database and used as a reference for tracing future leak tracing events.

In some embodiments, after the gas leak source tracing described above is performed, and before the user or the device is sent to a location for field investigation (e.g., performing data measurement and validating the gas leakage based on the data measurement), the computing system may utilize fitted leak source information to generate a model (e.g., a validation plume model) and run certain simulations (e.g., a "history matching" simulation) using the model. Such simulation using the validation model may enable determining an actual leakage duration, because a gas leakage in an initial time period (e.g., 30 minutes, 1 hour, 2 hours, 3 hours, and 5 hours from actual starting time of the gas leakage) may not be detectable.

In some embodiments, a forward modeling may be used to create a source tracing data set. For example, a source tracing data set may be created by setting certain relevant parameters, such as $(x_s, y_s, z_s)=(25,20,1.0)$, $Q_s=1.5$ scf/min, leak time=day 66, and lagging time=24 hours. During this 24-hour interval, 9 effective measurements may be obtained and shown in a Table 4 shown below.

numerical gas concentration value bar 212 is used herein to indicate different contour line with a corresponding value.

Figure 12A:
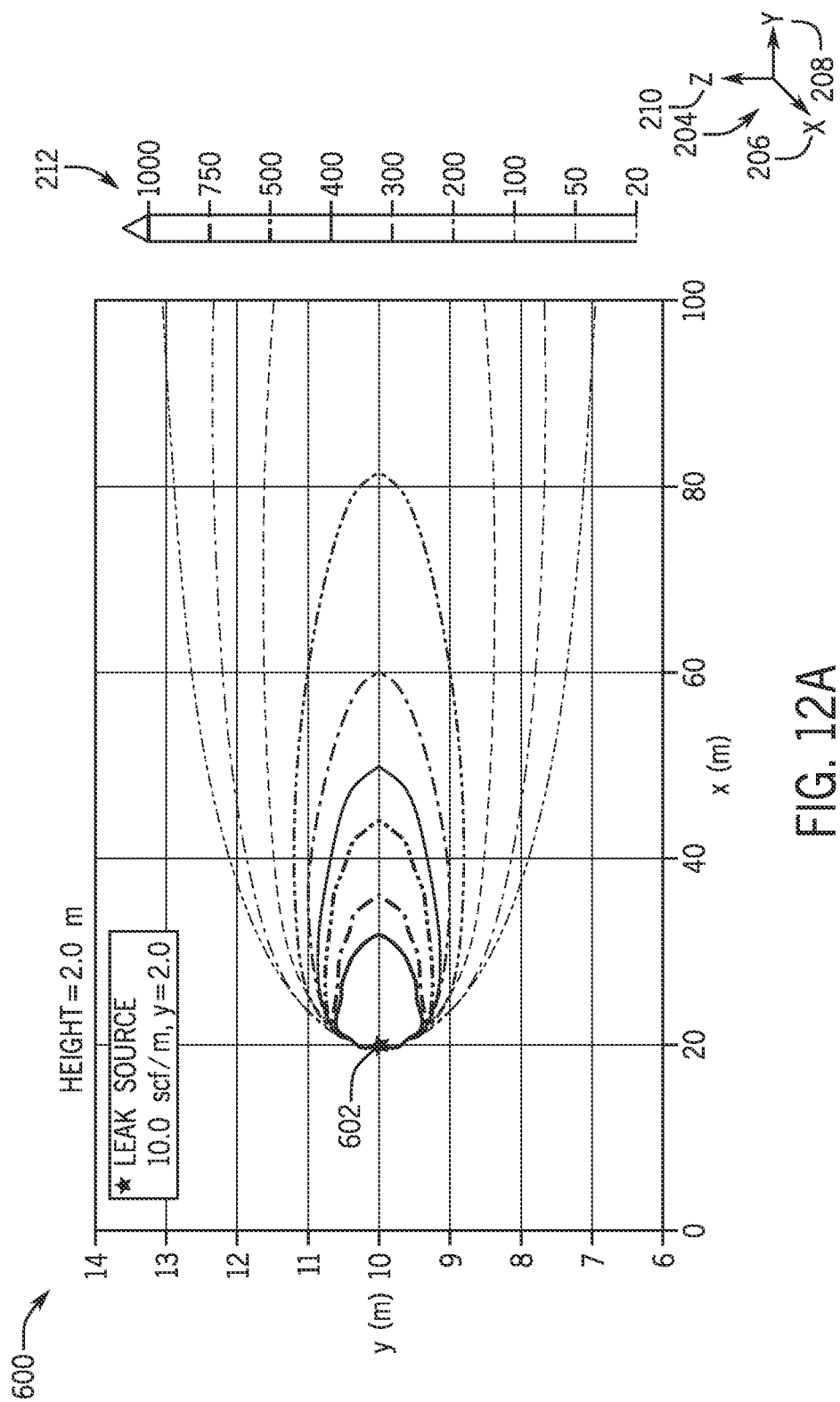
FIG. 12A is an example contour plot in a first plane (X and Y) of a plume distribution from a single leak source, in accordance with embodiments of the present disclosure.

With this in mind, FIG. 12A is an example contour plot 600 in a first plane (X-Y) of a plume distribution from a single leak source 602. The first plane consists of X and Y-axes of the coordinate system 204 at a height of z=2 meters. The leak source 602 releases leaking gas at a flow rate of 10.0 SCP/M. Each contour line may represent gas concentration variations (e.g., decreasing) with each contour line further away from the leak source 602 in the first plane.

Figure 12B:
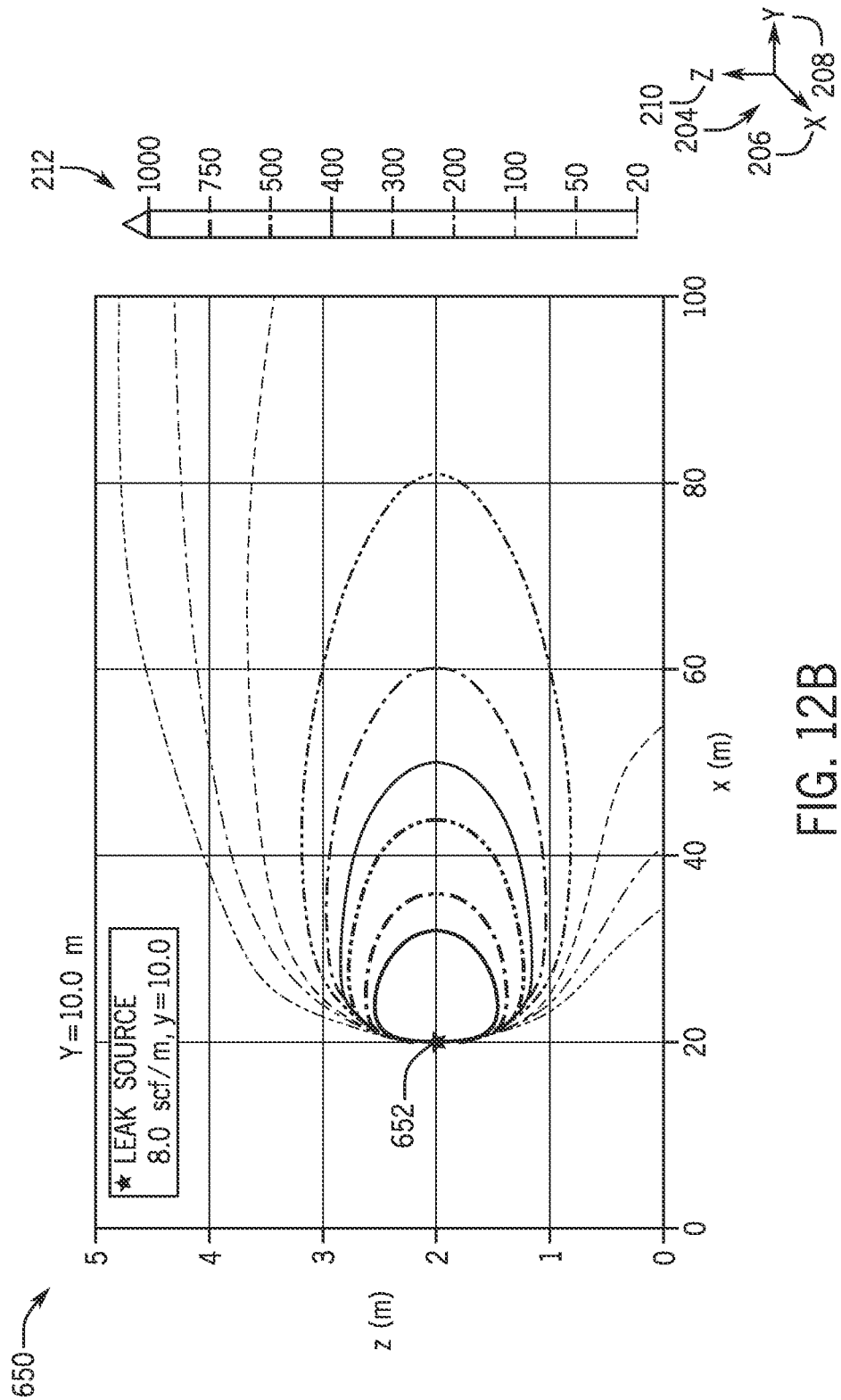
FIG. 12B is an example contour plot in a second plane (X and Z) of the plume distribution from the single leak source, in accordance with embodiments of the present disclosure.

FIG. 12B is an example contour plot 650 in a second plane (X-Z) of the plume distribution from a single leak source 652. The second plane consists of X and Z-axes of the coordinate system 204 at y=10 meters. The leak source 652 releases leaking gas at a flow rate of 8.0 SCP/M. Each contour line may represent gas concentration variations (e.g., decreasing) with each contour line further away from the leak source 652 in the first plane.

Figure 12C:
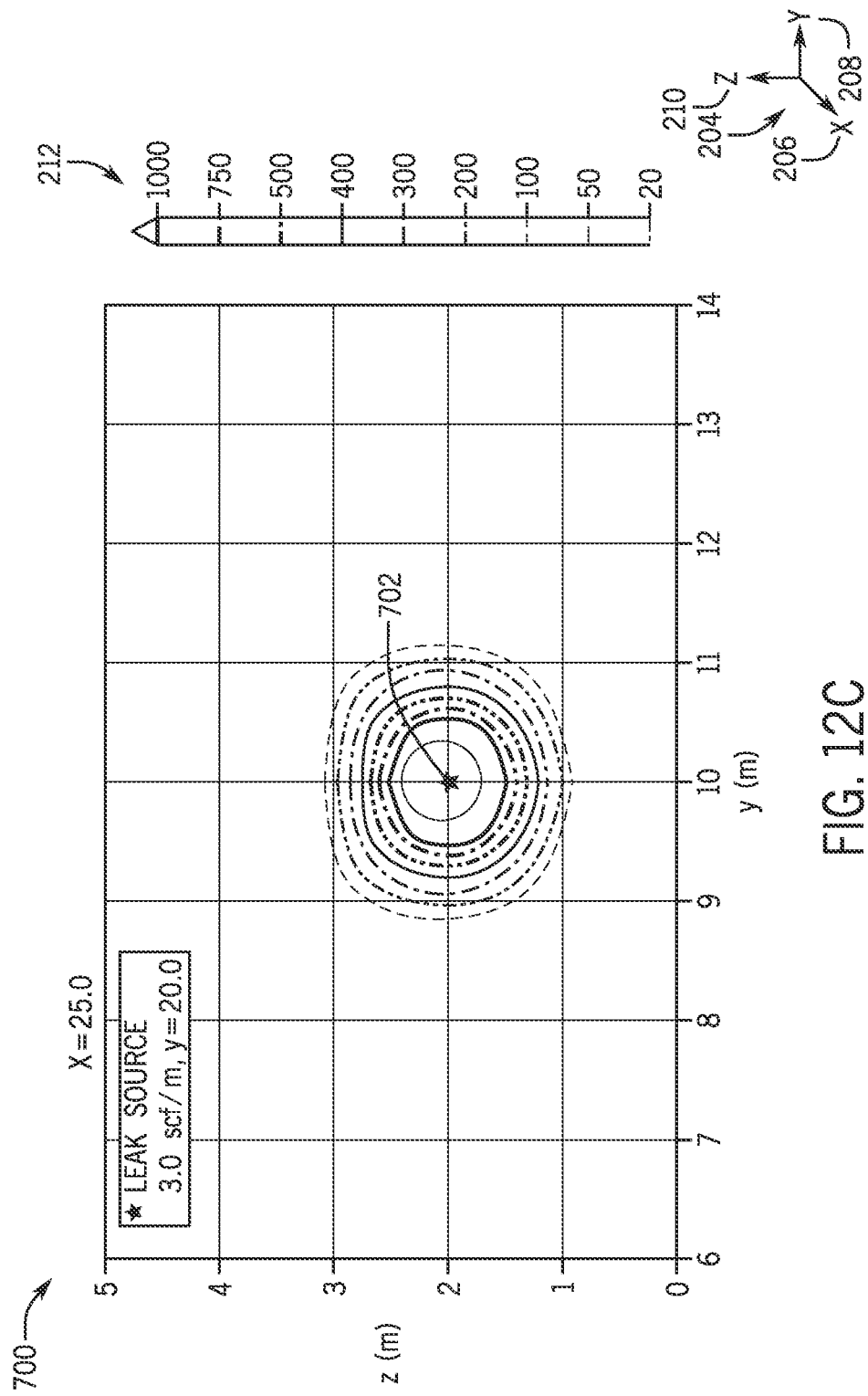
FIG. 12C is an example contour plot in a third plane (Y and Z) of the plume distribution from the single leak source, in accordance with embodiments of the present disclosure.

FIG. 12C is an example contour plot 700 in a third plane (Y-Z) of the plume distribution from a single leak source 702. The third plane consists of Y and Z-axes of the coordinate system 204 at x=25 meters. The leak source 702 releases leaking gas at a flow rate of 3.0 SCP/M. Each contour line may represent gas concentration variations (e.g., decreasing) with each contour line further away from the leak source 702 in the first plane.

FIGS. 12A-12C illustrate different gas plume distributions (e.g., contour plots 600, 650, and 700) from different leak sources (e.g., leak sources 602, 652, and 702) in different planes (e.g., planes X-Y, X-Z, and Y-Z). Such figures may enable a user to view the calculated (e.g., using the Gaussian gas plume model) gas concentrations at different locations with respect to the locations of the leak sources in quantitative displays.

To further illustrate the example method 550 for gas leak source tracing of FIG. 11, an example of a sample analysis program (e.g., a software program as a part of the green-

TABLE 4

| Sample # (i) | Time ($t_i$) | Wind speed ($U_i$) | Wind Direction ($\theta_i$) | Receptor X ($x_i$) | Receptor Y ($y_i$) | Receptor Z ($z_i$) | Receptor C ($\tilde{C}$) | Actual C (C) |
|---|---|---|---|---|---|---|---|---|
| 0 | 2020 Mar. 6 01:50:00 | 1.937127 | 332.0 | 27.5 | 15.0 | 1.5 | 347.894118 | 307.631992 |
| 1 | 2020 Mar. 6 09:20:00 | 0.622648 | 149.0 | 22.5 | 25.0 | 1.5 | 545.765663 | 501.748857 |
| 2 | 2020 Mar. 6 09:30:00 | 0.622648 | 149.0 | 22.5 | 25.0 | 1.5 | 485.143526 | 501.748857 |
| 3 | 2020 Mar. 6 09:40:00 | 0.622648 | 149.0 | 22.5 | 25.0 | 1.5 | 505.818865 | 501.748857 |
| 4 | 2020 Mar. 6 12:30:00 | 1.591211 | 156.0 | 22.5 | 25.0 | 1.5 | 419.808419 | 391.824740 |
| 5 | 2020 Mar. 6 13:10:00 | 2.144676 | 155.0 | 22.5 | 25.0 | 1.5 | 279.710733 | 254.104451 |
| 6 | 2020 Mar. 6 16:30:00 | 0.968563 | 154.0 | 22.5 | 25.0 | 1.5 | 950.721248 | 923.426086 |
| 7 | 2020 Mar. 6 23:30:00 | 1.522028 | 34.0 | 27.5 | 15.0 | 1.5 | 494.966931 | 490.310927 |
| 8 | 2020 Mar. 6 23:40:00 | 1.522028 | 334.0 | 27.5 | 15.0 | 1.5 | 513.815013 | 490.310927 |

In Table 4, note that C is the actual modeled concentration and unknown in the source tracing problem, the receptor measurement error $|C(x_i, y_i, z_i)-\tilde{C}_i|$ is taken as a random number between 0 and 50 ppm in present example.

Figure 13:
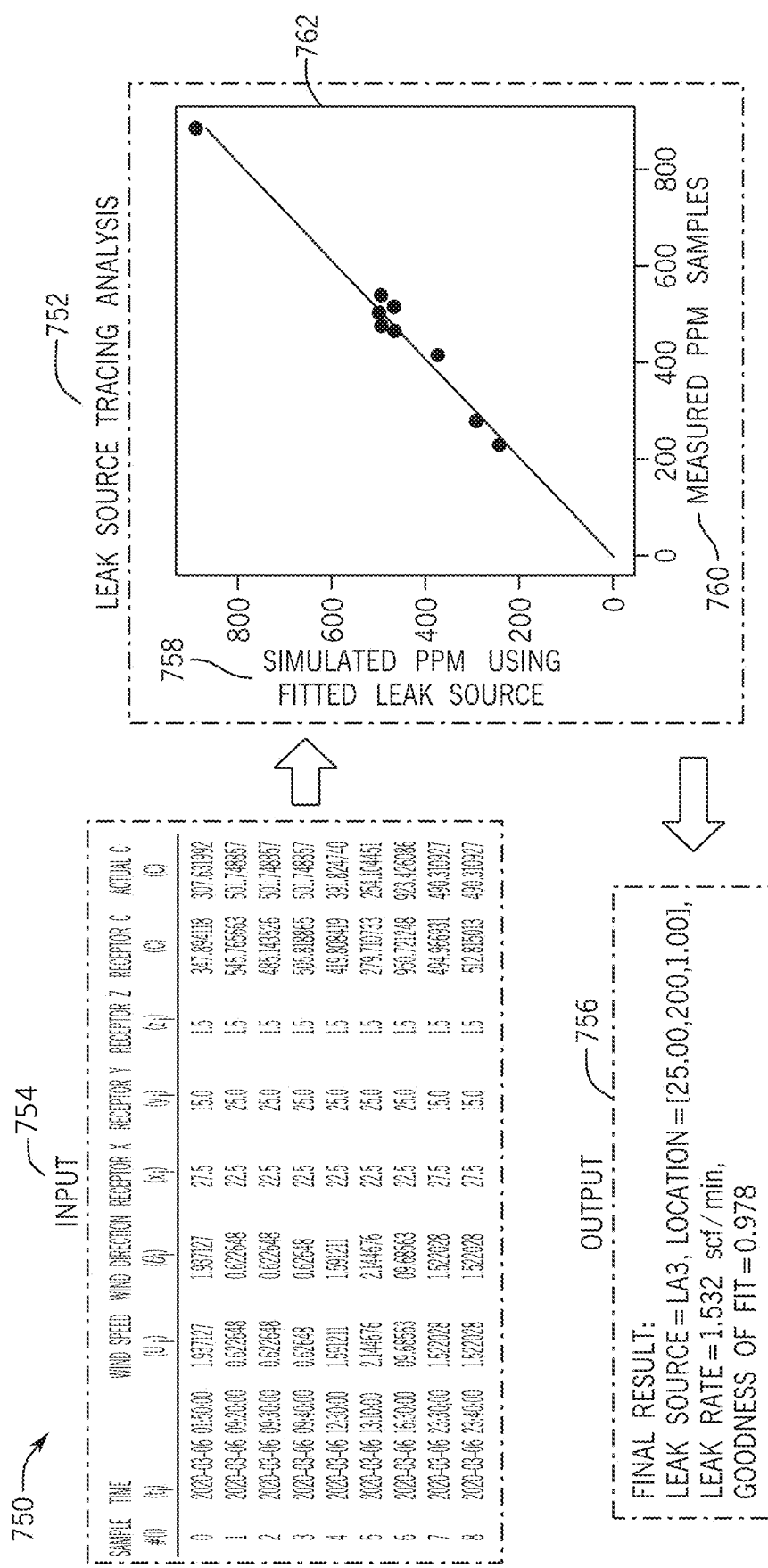
FIG. 13 is an example of simulation output using the gas leak source tracing workflow of FIG. 11, in accordance with embodiments of the present disclosure.

Each of the following figures, such as FIGS. 12A, 12B, and 12C, illustrates a gas plume distribution from a single leak source in different planes. A Gaussian gas plume model is used to compute each gas concentration distribution plot corresponding to a respective plane (e.g., X-Y, Y-Z), which displays the calculated extent of the plume distribution in the respective plane. Each contour line in a gas concentration distribution plot quantitatively represents a calculated (e.g., using the Gaussian gas plume model) gas concentration at a location with respect to the location of the leak source. The house gas emission monitoring system 50) is presented. FIG. 13 is an example of a leak source tracing analysis 750 with simulation input and output using the example method 550. The leak source tracing analysis 750 includes a leak source tracing analysis program 752 that receives input 754, performs leak source tracing analysis as described above in process blocks 552-564, and generates output 756.

In the present example, the leak source tracing analysis program 752 receives the input 754 that may include current time (e.g., date, hour, minute, second) and estimated leakage duration (e.g., 21 hours). The input 754 may also include 9 candidate leak sources with corresponding leak rate (e.g., leak source LA1 with leak rate 5.00 scf/min, leak source LB with leak rate 10.00 scf/min, leak source LE2 with leak rate 5.00 scf/min). The leak source tracing analysis program 752 then analyzes a potential for each candidate leak source marked during the sensor planning phase, estimates the best-fit leakage rate and corresponding goodness-of-fit metrics (e.g., using the $R^2$ goodness-of-fit indicator). In certain embodiments, the interpreted leak location may be exact, while the computed leak rate is 1.532 scf/min as opposed to 1.5 scf/min that is defined in the data setup (e.g., setup gas sensor placement planning). The difference between the computed leak rate and defined leak rate in the data setup is caused by a +50 ppm measurement error artificially introduced to the sensor data.

A comparison of simulated concentration 758 versus measured concentration 760 is plotted in a plot 762. In the present example, only one parameter, the leak rate $Q_s$, is optimized. Based on the optimization, the leak source tracing analysis program 752 may create the output 756 including an identified leak source (e.g., leak source LA3) with source location coordinates (e.g., x=25 m, y=200 m, z=1 m), leak rate (e.g., 1.532 scf/min) and goodness of fit (e.g., 0.978).

The optimization of one parameter $Q_s$ may have better performance (e.g., robustness, accuracy) than an optimization of the 4-parameter ($x_s$, $y_s$, $z_s$, $Q_s$). In certain cases where there are limited data samples (e.g., 2 or 3 valid concentration detection samples), the leak source tracing analysis program 752 may still generate desired output 756. In comparison to cases where the 4-parameter ($x_s$, $y_s$, $z_s$, $Q_s$) are optimized, a 4-parameter search may have at least 4 data samples as input to launch optimization algorithms. As such, the one parameter (leak rate $Q_s$) optimization may be desirable when, for example, the early detection of leakage is of priority.

Figure 14:
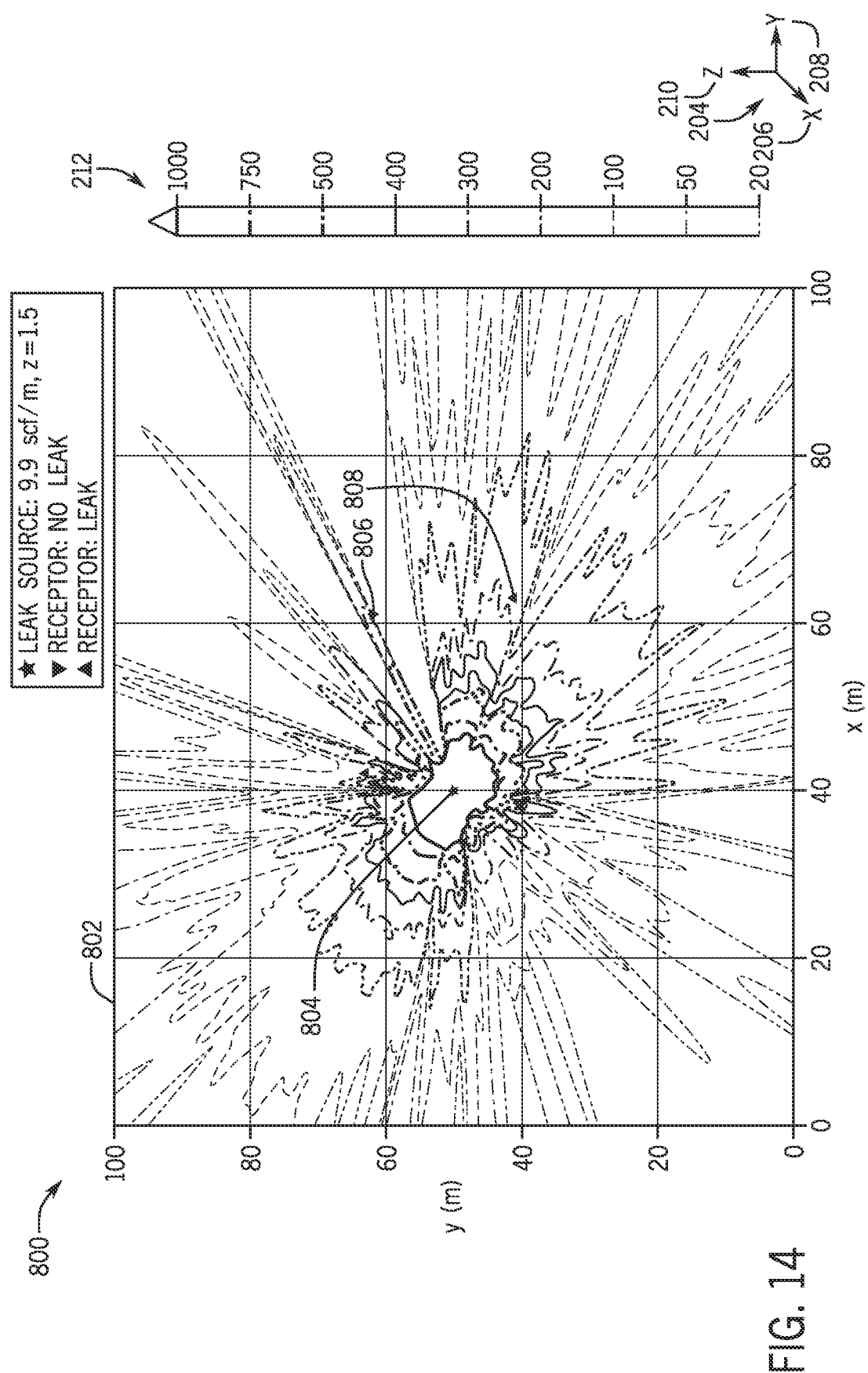
FIG. 14 is an example of a history matching procedure to validate the result of the source tracing method of FIG. 11, in accordance with embodiments of the present disclosure.

FIG. 14 is an example of a history matching procedure 800 to validate the result of the source tracing method 550 of FIG. 11. The present example illustrates how to use fitted leak source information to generate a validation or history matching scenario that may be used to further validate the result of the source tracing method 550. Additionally, the history matching procedure 800 may be used to refine a leakage time estimation result. The history matching procedure 800 includes plotting gas concentration values in a contour plot 802 (e.g., in an X-Y plane). The star indicates a leak source 804. The contour plot 802 is generated from a grid point evaluation, while the peak concentration at each sensor location is shown by the text next to a sensor. For example, a Gaussian gas plume model may be used to compute the gas contour plot 802, which displays the calculated extent of the plume distribution in the X-Y plane. Each of the illustrated contour lines quantitatively represents a calculated gas concentration profile at locations with respect to the location of a leak source 804. Each contour line may represent gas concentration variations (e.g., decreasing) with each contour line further away from the leak source 804. A numerical gas concentration value bar 212 is used herein to indicate different contour line with a corresponding value.

During a gas leak source tracing process, if a sensor (e.g., sensor 806) does not detect a gas leakage, a downward triangle is used to indicate the sensor in the contour map 802. If a sensor (e.g., sensor 808) detects a gas leakage, an upward triangle is used to indicate the sensor in the contour map 802.

Figure 15:
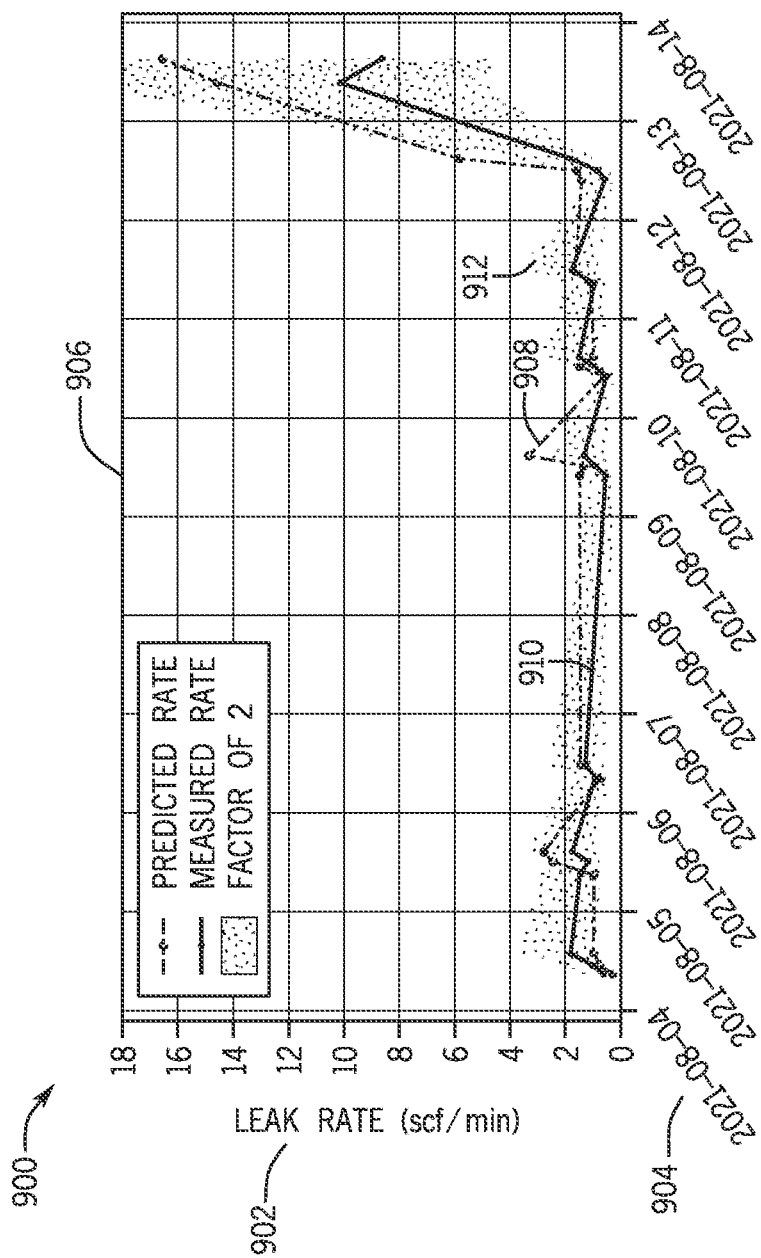
FIG. 15 is an example of validating leak source quantification algorithms using a controlled release experiment, in accordance with embodiments of the present disclosure.

FIG. 15 is an example of validating leak source quantification algorithms 900 described above using a controlled release experiment. A field test at the METEC test site of Colorado State University was conducted during Aug. 2 to Aug. 13, 2021. The field test includes 21 controlled release experiments. The gas leak rate 902 versus measurement time 904 is plotted in a plot 906. In the plot 906, a curve 908 represents predicted gas release rate, a curve 910 represents actual gas release rate measured with a flowmeter, and a shadow 912 represents rate ranges within a factor of 2 for each experiment, wherein measurement units are in scf/min.

Based on the field test result presented in the plot 906, the leak source quantification algorithms appear to be robust even without any tuning parameter. For example, in 20 out of 21 controlled release experiments, the leak source quantification algorithms identify the exact leak sources, with one exception that has an offset distance of 3.4 meters. Moreover, the leak source quantification algorithms quantify the leak rate within a factor of 3, with one exception that has an offset by a factor of 3.2. Among 21 controlled release experiments, 72% of the experiments quantify the leak rate within a factor of 2. It should be noted that these controlled release experiments were conducted with a relatively close distance between sensors and gas leak sources (e.g., 10-25 meters). In certain cases, interpretation errors may increase with larger distances (e.g., 50, 75, or 100 meters).

The techniques presented herein relate to systems and methods to perform green gas (e.g., methane, carbon oxides, nitrogen oxides, and ozone) leakage detection sensor placement, leakage source location and quantification for any suitable facilities (e.g., oil and gas production facilities). The techniques presented herein provide the systems and methods for monitoring gas leakage across a large area or an entire facility with optimized sensor deployment planning, which may reduce capital cost and bring encouraging returns. The illustrated systems and methods enable systematic solutions based on numerical modeling, such as planning the locations of greenhouse gas leakage detection sensors in an optimized way, such that the sensor deployment plan may cover as many potential leak sources in a facility as possible while maintaining economic budget.

The specific embodiments described above have been illustrated by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform] ing [a function] . . . " or "step for [perform] ing [a function] . . . ", it is intended that such elements are to be interpreted under 35 U.S.C. 112 (f). However, for any claims containing elements designated in any other manner, it is intended that such elements are not to be interpreted under 35 U.S.C. 112 (f).

While only certain features of the embodiments described herein have been illustrated and described, many modifications and changes will occur to those skilled in the art. It is, therefore, to be understood that the appended claims are intended to cover all such modifications and changes as fall within the true spirit of the embodiments described herein.

The invention claimed is:

1. A gas emission analysis (GEA) system, comprising:
one or more memories configured to store a digital representation of a worksite comprising a gas plume model; and one or more processors configured to execute instructions stored in the one or more memories to perform actions comprising:
    receiving input data from a plurality of data sources comprising at least a plurality of sensors;
    determining one or more potential sensor locations associated with the plurality of sensors using the gas plume model based on the input data;
    generating a plurality of candidate sensor deployment plans based on the one or more potential sensor locations;
    determining a sensor deployment plan from the plurality of candidate sensor deployment plans using the gas plume model based at least in part on plan coverage ratios and plan cost associated with the plurality of candidate sensor deployment plans;
    deploying the plurality of sensors based on the sensor deployment plan;
    setting one or more gas leakage event trigger logics for a subset of the plurality of sensors;
    receiving updated input data from the plurality of data sources;
    determining whether at least a portion of the input data activates at least one of the one or more gas leakage event trigger logics;
    receiving a list of effective gas concentration measurements from the subset of the plurality of sensors associated with a plurality of potential gas leak sources;
    generating a plurality of estimation metrics based on one or more gas concentration simulations;
    ranking the plurality of potential gas leak sources based on the plurality of estimation metrics; and
    generating a recommendation configured to prompt a user or a device to deploy a detector to the worksite based on the recommendation.

2. The GEA system of claim 1, wherein the one or more gas leakage event trigger logics are set during a sensor setting phase for the subset of the plurality of sensors, wherein when a reading of a sensor of the plurality of sensors is above a threshold, the GEA system automatically triggers a gas leak source tracing for determining a gas leak source.

3. The GEA system of claim 1, wherein the list of effective gas concentration measurements comprise sensor location data, gas concentration readings associated with time stamps, wind speed, wind direction at the time stamps, and coordinates associated with the plurality of potential gas leak sources.

4. The GEA system of claim 1, wherein the plurality of potential gas leak sources are determined using the digital representation based at least in part on a history of gas leakages being detected at the worksite, and synthetic data from simulation data based on modeling various gas leakage events associated with the worksite.

5. The GEA system of claim 1, wherein the plurality of estimation metrics are generated based on simulated gas concentrations versus measured gas concentrations, wherein the plurality of estimation metrics are used to estimate at least a gas flow rate.

6. The GEA system of claim 1, wherein the plurality of estimation metrics comprises regression metrics or R2 goodness-of-fit indicators.

7. The GEA system of claim 1, wherein at least one of the plurality of sensors is configured to be deployed by the user or the robotic device, wherein the robotic device comprise an unmanned vehicle or a drone.

8. The GEA system of claim 1, wherein the recommendation comprises one or more locations associated with one or more of the plurality of potential gas leak sources.

9. The GEA system of claim 8, wherein the detector is configured to perform data measurement and validate a gas leakage at the one or more locations based on the data measurement.

10. The GEA system of claim 1, wherein determining the one or more potential sensor locations or determining the sensor deployment plan comprises interactive guided sensor placement using one or more interactive functions configured to support data analysis, data processing, and data simulations associated with gas emissions based on the input data, wherein the plurality of interactive functions comprises data mining, numerical calculation, modeling, machine learning, prediction, estimations, error analysis, and data visualization.

11. The GEA system of claim 1, wherein the digital representation includes a virtual representation of the worksite in a computational environment, wherein the virtual representation is updated using the updated input data, and wherein the virtual representation of the worksite is configured to use the gas plume model to perform simulations, machine learning, and data reasoning based on the updated input data.

12. The GEA system of claim 1, wherein the plurality of sensors comprises one or more gas sensors, one or more Optical Gas Imaging (OGI) cameras, and one or more meteorological sensors communicatively coupled to the GEA system.

13. The GEA system of claim 12, wherein the one or more gas sensors comprise gas composition sensors, gas specific sensors, noise or acoustic sensors, flow rate sensors, pressure sensors, wind sensors, temperature sensors, light sensors, flame sensors, flare monitors, tank sensors, gas concentration monitors, compressor health monitors, structural monitors, pipeline monitors, any other type of sensors capable of providing data related to gas emissions, or any combination thereof.

14. The GEA system of claim 1, comprising a user interface (UI) configured to enable the user to:
    interactively change a plurality of parameters comprising gas leak source identifications, gas leak time, and lagging time;
    view one or more peak concentration distributions instantaneously in response to changing the plurality of parameters; and
    modify one or more indicators associated with one or more sensors of the plurality of sensors that detected a gas leakage at the worksite.

15. A method comprising:
    receiving input data from a plurality of sensors;
    determining one or more potential sensor locations associated with the plurality of sensors using a gas plume model based on the input data;
    generating a plurality of candidate sensor deployment plans based on the one or more potential sensor locations;
    determining a sensor deployment plan from the plurality of candidate sensor deployment plans using the gas plume model based at least in part on plan coverage ratios and plan cost associated with the plurality of candidate sensor deployment plans;
    deploying the plurality of sensors based on the sensor deployment plan;
    setting one or more gas leakage event trigger logics for a subset of the plurality of sensors;

receiving updated input data from the plurality of sensors;
determining whether at least a portion of the input data activates at least one of the one or more gas leakage event trigger logics;
receiving a list of effective gas concentration measurements from the subset of the plurality of sensors associated with a plurality of potential gas leak sources;
generating a plurality of estimation metrics based on one or more gas concentration simulations;
ranking the plurality of potential gas leak sources based on the plurality of estimation metrics; and
generating a recommendation configured to prompt a user or a device to deploy a detector to a worksite based on the recommendation.

16. The method of claim 15, wherein the gas plume model is generated using one or more mathematic algorithms associated with data analysis, data processing, data simulations, and data correlations related to a gas emission.

17. The method of claim 16, wherein the gas emission comprises a gas distribution, a gas concentration, and a gas flow detection associated with a greenhouse gas released from the worksite.

18. The method of claim 17, wherein the greenhouse gas comprises methane.

19. The method of claim 16, wherein the data processing comprises image processing, wherein the image processing comprises at least image filtering, Fourier transformation, and pattern recognition based on image data acquired by Optical Gas Imaging (OGI) cameras.

20. The method of claim 16, wherein the data correlations comprise correlating sensor data acquired by the plurality of sensors with location data, time data, and weather data.

21. A non-transitory, computer-readable medium storing instructions that, when executed by one or more processors, are configured to cause the one or more processors to perform operations comprising:
deploying a plurality of sensors based on a sensor deployment plan;
setting one or more gas leakage event trigger logics for the plurality of sensors;
receiving input data from a plurality of data sources comprising the plurality of sensors;
determining whether at least a portion of the input data activates at least one of the one or more gas leakage event trigger logics;
receiving a list of effective gas concentration measurements from a subset of the plurality of sensors associated with a plurality of potential gas leak sources;
generating a plurality of estimation metrics based on one or more gas concentration simulations;
ranking the plurality of potential gas leak sources based on the plurality of estimation metrics; and
generating a recommendation configured to prompt a user or a device to deploy a detector to a worksite based on the recommendation.

22. The non-transitory, computer-readable medium of claim 21, wherein ranking the plurality of potential gas leak sources comprises:
sorting the plurality of potential gas leak sources; and
generating a ranking list comprising one or more candidates along with estimated gas leakage rate.

* * * * *